United States Patent
Du et al.

(10) Patent No.: US 12,070,462 B2
(45) Date of Patent: Aug. 27, 2024

(54) SETBP1 INHIBITORS FOR THE TREATMENT OF MYELOID NEOPLASMS AND SOLID TUMORS

(71) Applicant: The Henry M. Jackson Foundation for the Advancement of Military Medicine, Inc., Bethesda, MD (US)

(72) Inventors: Yang Du, Bethesda, MD (US); Nhu Nguyen, Bethesda, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 840 days.

(21) Appl. No.: 17/057,063

(22) PCT Filed: May 22, 2019

(86) PCT No.: PCT/US2019/033526
§ 371 (c)(1),
(2) Date: Nov. 19, 2020

(87) PCT Pub. No.: WO2019/226773
PCT Pub. Date: Nov. 28, 2019

(65) Prior Publication Data
US 2021/0205306 A1  Jul. 8, 2021

Related U.S. Application Data

(60) Provisional application No. 62/676,128, filed on May 24, 2018.

(51) Int. Cl.
| | | |
|---|---|---|
| A61K 31/517 | (2006.01) | |
| A61K 31/475 | (2006.01) | |
| A61P 35/00 | (2006.01) | |
| C07K 14/47 | (2006.01) | |

(52) U.S. Cl.
CPC .......... *A61K 31/517* (2013.01); *A61K 31/475* (2013.01); *A61P 35/00* (2018.01); *C07K 14/4702* (2013.01)

(58) Field of Classification Search
CPC .............................. A61K 31/517; A61P 35/00
See application file for complete search history.

(56) References Cited

U.S. PATENT DOCUMENTS

| | | |
|---|---|---|
| 4,698,423 A | 10/1987 | Honda et al. |
| 5,272,146 A | 12/1993 | Haugwitz et al. |
| 9,550,769 B2 | 1/2017 | Disney et al. |
| 9,920,058 B2 | 3/2018 | Srinivasan et al. |
| 10,011,598 B2 | 7/2018 | Disney et al. |
| 2009/0197906 A1 | 8/2009 | Auclair et al. |
| 2014/0329840 A1 | 11/2014 | Srinivasan et al. |

FOREIGN PATENT DOCUMENTS

| | | |
|---|---|---|
| WO | WO 2007/135538 A2 | 11/2007 |
| WO | WO 2020/247654 A1 | 12/2020 |

OTHER PUBLICATIONS

European Search Report and Opinion dated May 6, 2022 for EP Application No. 19808074.9. 10 pages.
Action, et al. Anticancer Specificity of Some Ellipticinium Salts against Human Brain Tumors in vitro. J. Med. Chem. 1994, 37, 14, 2185-2189.
Boven, et al. Phase II preclinical drug screening in human tumor xenografts: a first European multicenter collaborative study. Cancer Res (1992) 52 (21): 5940-5947.
International Search Report and Written Opinion dated Oct. 15, 2019 for PCT/US2019/033526, 10 pages.
Auclair, C. et al, "Physicochemical and Pharmacological Properties of the Antitumor Ellipticine Derivative 2-(Diethylamino-2-ethyl)9-hydroxy Ellipticinium-Chloride, HCI", Cancer Research, Dec. 1, 1987, vol. 47, No. 23, pp. 6254-6261.
Khayat, D et al., "Phase I study of Datelliptium chloride, hydrochloride given by 24-h continuous intravenous infusion", Cancer Chemotherapy and Pharmacology, vol. 30, No. 3, 1992, pp. 226-228.
Mucci-Lorusso, P et al., "Activity of Datelliptium acetate (NSC 311152; SR 95156A) against solid tumors of mice", Investigactional New Drugs, vol. 8, No. 3, Aug. 1990, pp. 253-261.

*Primary Examiner* — Golam M Shameem
(74) *Attorney, Agent, or Firm* — Sheppard Mullin Richter & Hampton LLP

(57) ABSTRACT

Chemical compounds for the treatment of myeloid neoplasms and solid tumors are described, where the compounds were identified through a screening process assessing the binding affinity of the compounds to a synthesized fragment of Setbp1 protein.

13 Claims, 21 Drawing Sheets

Specification includes a Sequence Listing.

Figure 18

Tag (containing 6x His)
MGSSHHHHHHSSGLVPRGSHMLEESHSEETIPSDSGIGTDNNSTSDQAEKSSESRRRYSFDFCSLDNPEAIPSDTSTKNRHG
HRQKHLIVDTFLAHESLKKPKHKRKSLQNRDDLQFLAELEELITKFQVFRISHRGYTFYHENPYPSIFRINFDQYYPVPYIQY
DPLLYLRRTSDLKSKKKRGRPAKTNDTMTKVPFLQGFSYPIPSGSYYAPYGMPYTSMPMMNLGYYGQYPAPLY Total of 5 injections indicated by dotted lines

SEQUENCE LISTING

<160> NUMBER OF SEQ ID NOS: 11

<210> SEQ ID NO 1
<211> LENGTH: 240
<212> TYPE: PRT
<213> ORGANISM: Artificial Sequence
<220> FEATURE:

<223> OTHER INFORMATION: Synthetic

<400> SEQUENCE: 1

```
Met Gly Ser Ser His His His His His His Ser Ser Gly Leu Val Pro
1               5                   10                  15

Lys Gly Ser His Met Leu Glu Glu Ser His Ser Glu Glu Thr Ile Pro
            20                  25                  30

Ser Asp Ser Gly Ile Gly Thr Asp Asn Asn Ser Thr Ser Asp Gln Ala
        35                  40                  45

Glu Lys Ser Ser Glu Ser Arg Arg Arg Tyr Ser Phe Asp Phe Cys Ser
    50                  55                  60

Leu Asp Asn Pro Glu Ala Ile Pro Ser Asp Thr Ser Thr Lys Asn Arg
65                  70                  75                  80

His Gly His Arg Gln Lys His Leu Ile Val Asp Thr Phe Leu Ala His
                85                  90                  95

Glu Ser Leu Lys Lys Pro Lys His Lys Arg Lys Arg Lys Ser Leu Gln
            100                 105                 110

Asn Arg Asp Asp Leu Gln Phe Leu Ala Glu Leu Glu Leu Ile Thr
        115                 120                 125

Lys Phe Gln Val Phe Arg Ile Ser His Arg Gly Tyr Thr Phe Tyr His
    130                 135                 140

Glu Asn Pro Tyr Pro Ser Ile Phe Arg Ile Asn Phe Asp Gln Tyr Tyr
145                 150                 155                 160

Pro Val Pro Tyr Ile Gln Tyr Asp Pro Leu Leu Tyr Leu Arg Arg Thr
                165                 170                 175

Ser Asp Leu Lys Ser Lys Lys Arg Gly Arg Pro Ala Lys Thr Asn
            180                 185                 190

Asp Thr Met Thr Lys Val Pro Phe Leu Gln Gly Phe Ser Tyr Pro Ile
        195                 200                 205

Pro Ser Gly Ser Tyr Tyr Ala Pro Tyr Gly Met Pro Tyr Thr Ser Met
    210                 215                 220

Pro Met Met Asn Leu Gly Tyr Gly Gln Tyr Pro Ala Pro Leu Tyr
225                 230                 235                 240
```

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tgtctcctct cccccaaacc                                           20

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
gagatgaggc ctgggattta ga                                        22

<210> SEQ ID NO 4
<211> LENGTH: 21
<212> TYPE: DNA
<213> ORGANISM: Artificial Sequence
<220> FEATURE:

```
<223> OTHER INFORMATION: Synthetic

<400> SEQUENCE: 4
ccagccctgg gtaaacttag c                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
cattgacctc aggccagaca                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
ccatgaaagc tcgggcttag                                                20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ctcgacatgg tgtcagttgt g                                              21

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
cctccctgga gaagagcta                                                 19

<210> SEQ ID NO 9
<211> LENGTH: 19
<212> TYPE: DNA
<213> ORGANISM: Artificial Sequence
<220> FEATURE:
<223> OTHER INFORMATION: Synthetic

<400> SEQUENCE: 9
tccataccca agaaggaag                                                 19

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
aggtcggtgt gaacggattt g                                              21
```

```
<210> SEQ ID NO 11
<211> LENGTH: 23
<212> TYPE: DNA
<213> ORGANISM: Artificial Sequence
<220> FEATURE:
<223> OTHER INFORMATION: Synthetic

<400> SEQUENCE: 11
tgtagaccat gtagttgagg tca                                            23
```

SETBP1 INHIBITORS FOR THE TREATMENT OF MYELOID NEOPLASMS AND SOLID TUMORS

CROSS-REFERENCE TO RELATED APPLICATIONS

This application is the U.S. national stage application of International Application No. PCT/US2019/033526, filed May 22, 2019, which claims the benefit under 35 U.S.C. § 119(e) to U.S. Provisional Application No. 62/676,128, filed May 24, 2018, each of which is incorporated by reference in its entirety.

STATEMENT REGARDING FEDERALLY SPONSORED RESEARCH OR DEVELOPMENT

This invention was made with government support under QP86GI and PED-86-9301 awarded by the Uniformed Services University of the Health Sciences (USUHS) and under 64349 awarded by Walter Reed National Military Medical Center (WRNMMC). The government has certain rights in the invention.

REFERENCE TO SEQUENCE LISTING

A computer readable text file, entitled "72YZ-314544-US_ST25.txt," created on or about May 27, 2021, with a file size of about 8 kb contains the sequence listing for this application and is hereby incorporated by reference in its entirety.

BACKGROUND

SET binding protein 1 (SETBP1) encodes a large AT-hook transcription factor of over 1500 amino acids and was first cloned in a screen to identify interacting factors for oncoprotein SET and is expressed in a wide variety of tissues including heart, brain, kidney, liver, lung, pancreas, spleen, and skeletal muscle (Minakuchi et al., Eur. J. Biochem. 268(5):1340-1351 (2001)). Its abnormal activation through overexpression or missense mutations has recently been found to occur frequently in a variety of human myeloid neoplasms, including primary acute myeloid leukemias (AMLs) (Cristobal et al., Blood 115(3):615-625 (2010)), chronic myeloid leukemia blast crisis (CML-BC) (Oakley et al., Blood 119(25):6099-6108 (2012)), atypical chronic myeloid leukemia (aCML) (Piazza et al., Nat. Genet. 45(1):18-24 (2013)), chronic myelomonocytic leukemia (CMML), secondary AML (sAML) (Makashima et al., Nat. Genet. 45(8):942-946 (2013)), juvenile myelomonocytic leukemia (JMML) (Sakaguchi et al., Nat. Genet. 45(8):937-941 (2013)), and myelodysplastic syndrome (MDS) (Damm et al., Leukemia 27(6):1401-1403 (2013); Fernandez-Mercado et al., Br. J. Haematol. 163(2):235-239 (2013)); and Hou et al., Am. J. Hematol. 89(2):181-186 (2014)).

SETBP1 activation likely plays an important role in driving the development of these diseases based on the observation that overexpression of either wild-type Setbp1 or its missense mutants has been shown to induce AML development in mice. SETBP1 activation has also been associated with a poor prognosis in many of these malignancies, suggesting an urgent need for developing effective targeted therapies for affected patients (Cristobal et al., Blood 115(3):615-625 (2010); Piazza et al., Nat. Genet. 45(1):18-24 (2013); and Makashima et al., Nat. Genet. 45(8):942-946 (2013)). Targeting SETBP1-induced transcriptional activation may represent a promising therapeutic strategy since transcriptional activation of Hoxa9, Hoxa10 and Myb by Setbp1 and its misense mutants has been shown to be essential for them to induce immortalization of normal mouse myeloid progenitors (Oakley et al., Blood 119(25):6099-6108 (2012); Nguyen et al., Oncotarget 7(52):86300-86312 (2016)). A more complete understanding of the molecular mechanisms of Setbp1-directed transcriptional regulation should facilitate the finding of effective targeted therapies for myeloid neoplasms with SETBP1 activation.

In contrast to its classical role in nuclear exportation (Fukuda et al., Nature 390(6657):308-311 (1997); Ossareh-Nazari et al., Science 278(5335):141-144 (1997); Hutten et al., Trends Cell. Biol. 17(4):193-201 (2007); and Turner et al., Curr. Med. Chem. 15(26):2648-2655 (2008)), it was observed by the inventors of the present application that Xpo1 (also known as CRM1) may be an essential co-factor for Setbp1 and Setbp1 missense mutants in activating the transcription of key targets including Hoxa9, Hoxa10, and Myb. A motif responsible for the interaction between Setbp1/Setbp1 misense mutants and Xpo1 was also identified and represents a therapeutic target for treating neoplasms with SETBP1 activation. Further, by carrying out a compound screen for small molecules which could interact with a Setbp1 peptide fragment encompassing this motif (referred to herein as "polypeptide 25-20"), chemical compounds capable of inhibiting the growth of myeloid progenitors immortalized by Setbp1 or its missense mutants and also reducing Setbp1 target gene transcription in these cells were identified. The identification and therapeutic use of these compounds for treating myeloid neoplasms and other cancers, such as solid tumor cancers, with SETBP1 activation are described herein.

SUMMARY OF THE INVENTION

An aspect of the invention is a method for treating a myeloid neoplasm or a solid tumor in a subject, comprising administering to a subject in need thereof a therapeutically effective amount of a compound of Formula (1):

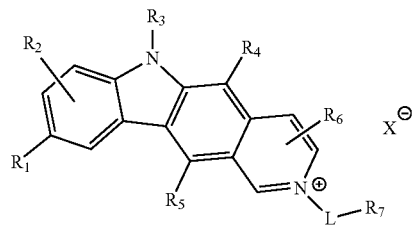

or a pharmaceutically acceptable salt thereof, wherein
$R_1$ is —$OR_5$, —$SR_8$ or —$NR_8R_5$;
$R_2$, $R_3$, $R_4$, $R_5$ and $R_6$ are independently H or $C_{1-4}$alkyl;
$R_7$ is —$NR_{10}R_{10}$ or a heterocyclyl group;
L is —$(CR_9R_9)_n$—;
$X^-$ is an organic or inorganic anion;
each $R_8$ is independently H or $C_{1-3}$ alkyl;
each $R_9$ is independently H or $C_{1-3}$ alkyl;
each $R_{10}$ is independently H or $C_{1-3}$ alkyl; and
n is 1, 2, 3 or 4.

In an exemplary embodiment, the subject is a human.

In an exemplary embodiment, the method is for treating a myeloid neoplasm while in another embodiment, the method is for treating a solid tumor.

In an exemplary embodiment of Formula (1), $R_1$ is $-OR_8$.

In an exemplary embodiment of Formula (1), $R_1$ is $-OR_8$ and $R_3$ is H.

In an exemplary embodiment of Formula (1), $R_1$ is $-OR_8$, $R_3$ is H, $R_8$ is H and each $R_9$ is H.

In an exemplary embodiment of Formula (1), n is 2.

In an exemplary embodiment of Formula (1), $R_1$ is $-OR_8$ and at least one $R_9$ is H.

In an exemplary embodiment of Formula (1), $R_1$ is $-NR_8R_8$, $R_3$ is H, each $R_8$ is H and each $R_9$ is H.

In an exemplary embodiment of Formula (1), at least one of $R_4$ and $R_5$ is $-CH_3$.

In an exemplary embodiment of Formula (1), each of $R_4$ and $R_5$ is $-CH_3$.

In an exemplary embodiment of Formula (1), $R_1$ is $-OR_8$, $R_2$ is H, $R_3$ is H and each of $R_4$ and $R_5$ is $-CH_3$.

In an exemplary embodiment of Formula (1), $R_7$ is a heterocyclyl group, where the heterocyclyl group is a 5- or 6-membered ring containing 1 or 2 nitrogen atoms.

In an exemplary embodiment of Formula (1), $R_7$ is a heterocyclyl group, $R_2$ is H and $R_1$ is $-OR_8$.

In an exemplary embodiment of Formula (1), $R_7$ is a heterocyclyl group, $R_2$ is H, $R_1$ is $-OR_8$ and $R_3$ is H.

In an exemplary embodiment of Formula (1), $R_7$ is a heterocyclyl group where the heterocyclyl group is a piperidinyl group, $R_1$ is $-OR_8$, $R_2$ is H, $R_3$ is H, $R_8$ is H and each $R_9$ is H.

In an exemplary embodiment of Formula (1), $R_7$ is a heterocyclyl group where the heterocyclyl group is a piperidinyl group, $R_2$ is H and at least one $R_9$ is H.

In an exemplary embodiment of Formula (1), $R_7$ is a heterocyclyl group where the heterocyclyl group is a piperidinyl group, $R_2$ is H and each $R_9$ is H.

In an exemplary embodiment of Formula (1), $R_7$ is a heterocyclyl group where the heterocyclyl group is a piperidinyl group, $R_2$ is H and at least one of $R_4$ and $R_5$ is $-CH_3$.

In an exemplary embodiment of Formula (1), $R_7$ is a heterocyclyl group where the heterocyclyl group is a piperidinyl group, $R_2$ is H and each of $R_4$ and $R_5$ is $-CH_3$.

In an exemplary embodiment of Formula (1), $R_7$ is a heterocyclyl group where the heterocyclyl group is a piperidinyl group, $R_1$ is $-OR_8$, $R_2$ is H, $R_3$ is H and each of $R_4$ and $R_5$ is $-CH_3$.

In an exemplary embodiment of Formula (1), X is F, Cl, Br or I.

In an exemplary embodiment of Formula (1), $R_7$ is a heterocyclyl group where the heterocyclyl group is a piperidinyl group, $R_1$ is $-OR_8$, $R_2$ is H, $R_3$ is H, each of $R_4$ and $R_5$ is $-CH_3$ and X is F, Cl, Br or I.

In an exemplary embodiment of Formula (1), $R_7$ is $-NR_{10}R_{10}$.

In an exemplary embodiment of Formula (1), $R_7$ is $-NR_{10}R_{10}$ and each $R_{10}$ is independently $C_{1-3}$ alkyl.

In an exemplary embodiment of Formula (1), $R_7$ is $-NR_{10}R_{10}$ and one $R_{10}$ is $C_{1-3}$ alkyl and one $R_{10}$ is $-H$.

In an exemplary embodiment of Formula (1), $R_2$ is H, $R_7$ is $-NR_{10}R_{10}$ and each $R_{10}$ is $-CH_2CH_3$.

In an exemplary embodiment of Formula (1), $R_2$ is H, $R_7$ is $-NR_{10}R_{10}$ and each $R_{10}$ is H.

In an exemplary embodiment of Formula (1), $R_2$ is H, $R_7$ is $-NR_{10}R_{10}$, $R_1$ is $-OR_8$ and $R_3$ is H.

In an exemplary embodiment of Formula (1), $R_2$ is H, $R_7$ is $-NR_{10}R_{10}$, $R_1$ is $-OR_8$, $R_3$ is H, $R_8$ is H and each $R_9$ is H.

In an exemplary embodiment of Formula (1), $R_2$ is H, $R_7$ is $-NR_{10}R_{10}$ and at least one $R_9$ is H.

In an exemplary embodiment of Formula (1), $R_2$ is H, $R_7$ is $-NR_{10}R_{10}$ and each $R_9$ is H.

In an exemplary embodiment of Formula (1), $R_7$ is $-NR_{10}R_{10}$, each $R_{10}$ is $-CH_2CH_3$ and at least one of $R_4$ and $R_5$ is $-CH_3$.

In an exemplary embodiment of Formula (1), $R_2$ is H, $R_7$ is $-NR_{10}R_{10}$, each $R_{10}$ is $-CH_2CH_3$ and each of $R_4$ and $R_5$ is $-CH_3$.

In an exemplary embodiment of Formula (1), $R_2$ is H, $R_7$ is $-NR_{10}R_{10}$, each $R_{10}$ is $-CH_2CH_3$, $R_1$ is $-OR_8$, $R_3$ is H, each of $R_4$ and $R_5$ is $-CH_3$ and X is F, Cl, Br or I.

In an exemplary embodiment of Formula (1), $R_7$ is a heterocyclyl group selected from the group consisting of morpholinyl, pyrrolidinonyl, pyrrolidinyl, piperidinyl, piperazinyl and tetrahydropyranyl.

In an exemplary embodiment of Formula (1), $R_7$ is a heterocyclyl group selected from the group consisting of morpholinyl, piperidinyl, piperazinyl and tetrahydropyranyl.

In an exemplary embodiment of the compound of Formula (1), $R_1$ is $-OR_8$; $R_2$, $R_3$ and $R_6$ are H; $R_4$ and $R_5$ are independently $C_{1-3}$ alkyl; $R_7$ is $-NR_{10}R_{10}$ or a piperidinyl group; L is $-(CR_9R_9)_n-$; X is an organic or inorganic anion; $R_8$ is H or $C_{1-3}$ alkyl; each $R_9$ is independently H or $C_{1-3}$ alkyl; each $R_{10}$ is independently H or $C_{1-3}$ alkyl; and n is 1, 2, 3 or 4. In a particular embodiment, X is selected from the group consisting of F, Cl, Br and I. In another particular embodiment, n is 2.

In an exemplary embodiment of the compound of Formula (1), $R_1$ is $-OR_8$; $R_2$, $R_3$, $R_6$, $R_8$ and $R_9$ are H; $R_4$ and $R_5$ are $CH_3$; $R_7$ is a piperidinyl group; L is $-(CR_9R_9)_n-$; X is selected from the group consisting of F, Cl, Br and I; and n is 1, 2, 3 or 4.

In an exemplary embodiment of the compound of Formula (1), $R_1$ is $-OR_8$; $R_2$, $R_3$, $R_6$, $R_8$ and $R_9$ are H; $R_4$ and $R_5$ are $CH_3$; $R_7$ is $-NR_{10}R_{10}$; each $R_{10}$ is independently $C_{1-3}$ alkyl; L is $-(CR_9R_9)_n-$; X is selected from the group consisting of F, Cl, Br and I; and n is 1, 2, 3 or 4.

In an exemplary embodiment, the compound of Formula (1) is a compound of Formula (1A):

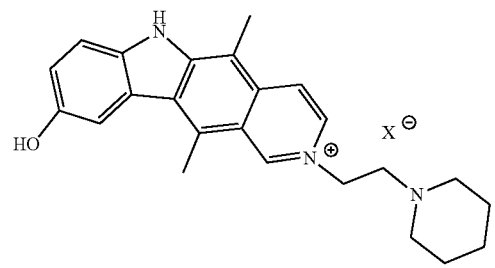

where X is an organic or inorganic anion. In an exemplary embodiment, X is selected from the group consisting of halo (F, Cl, Br, I), alkoxide, p-toluenesulfonate, methylsulfonate, sulfonate, phosphate, and carboxylate (such as benzoate, succinate, acetate, glycolate, maleate, malate, fumarate, citrate, tartrate, ascorbate, cinnamoate, mandeloate, and diphenylacetate). In a particular embodiment, X is selected from the group consisting of F, Cl, Br and I.

In an exemplary embodiment, the compound of Formula (1) is Compound (1AA):

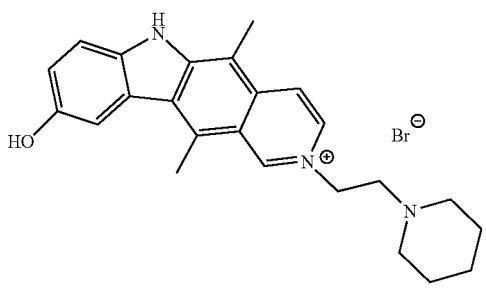

In an exemplary embodiment, the compound of Formula (1) is a compound of Formula (1B):

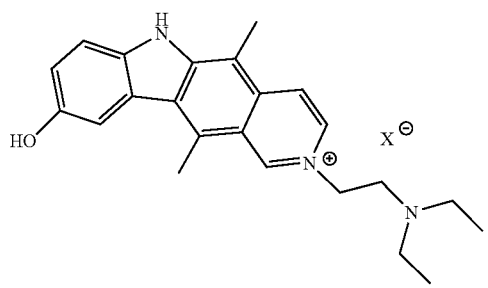

where X is an organic or inorganic anion. In an exemplary embodiment, X is selected from the group consisting of halo (F, Cl, Br, I), alkoxide, p-toluenesulfonate, methylsulfonate, sulfonate, phosphate, and carboxylate (such as benzoate, succinate, acetate, glycolate, maleate, malate, fumarate, citrate, tartrate, ascorbate, cinnamoate, mandeloate, and diphenylacetate). In a particular embodiment, X is selected from the group consisting of F, Cl, Br and I.

In an exemplary embodiment, the compound of Formula (1) is Compound (1BB):

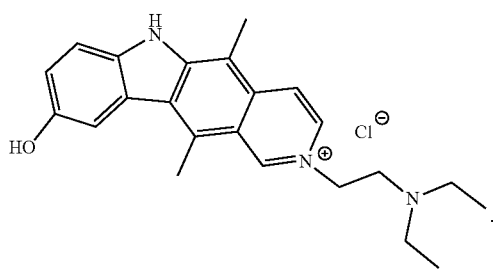 [SMILES: CCN(CC)CC[n+]1ccc2c(C)c3[nH]c4ccc(O)cc4c3c(C)c2c1 ; [Cl-]]

Another aspect of the invention is a method for treating a myeloid neoplasm or a solid tumor in a subject, comprising administering to a subject in need thereof a therapeutically effective amount of a compound of Formula (2):

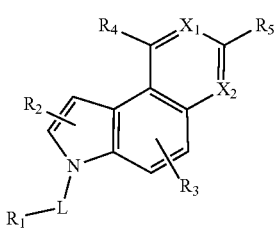

or a pharmaceutically acceptable salt thereof, wherein
$R_1$ is an aryl group or a heteroaryl group, where the aryl group and the heteroaryl group each has 0 to 3 substituents independently selected from the group consisting of —$NR_6R_6$, OH, F, Cl, Br and $C_{1-3}$ alkyl;
$R_2$ and $R_3$ are independently H or $C_{1-6}$alkyl;
$R_4$ and $R_5$ are independently H, —$NR_6R_6$ or $OR_6$;
each $R_6$ is independently H or $C_{1-3}$ alkyl;
$X_1$ and $X_2$ are independently CH or N;
L is —$(CR_7R_7)_n$—;
each $R_7$ is independently H or $C_{1-3}$ alkyl; and
n is 1, 2, 3 or 4.

In an exemplary embodiment, the subject is a human.

In an exemplary embodiment of Formula (2), the aryl or heteroaryl group of $R_1$ is selected from the group consisting of phenyl, furyl, benzofuranyl, thiophenyl, benzothiophenyl, pyrrolyl, pyridyl and pyrimidinyl.

In an exemplary embodiment of Formula (2), $R_1$ is a phenyl group having 1 substituent that is —$NR_6R_6$.

In an exemplary embodiment of Formula (2), $R_1$ is a phenyl group having 1 substituent that is —$NR_6R_6$ where at least one of $R_6$ is H.

In an exemplary embodiment of Formula (2), $R_1$ is a phenyl group having 1 substituent that is —$NR_6R_6$ where each $R_6$ is H.

In an exemplary embodiment of Formula (2), at least one of $R_2$ and $R_3$ is H.

In an exemplary embodiment of Formula (2), each of $R_2$ and $R_3$ is H.

In an exemplary embodiment of Formula (2), $X_1$ and $X_2$ are each N and at least one of $R_4$ and $R_5$ is —$NR_6R_6$.

In an exemplary embodiment of Formula (2), $X_1$ and $X_2$ are each N and each of $R_4$ and $R_5$ is —$NR_6R_6$.

In an exemplary embodiment of Formula (2), $X_1$ and $X_2$ are each N and at least one of $R_4$ and $R_5$ is —$NR_6R_6$ where each $R_6$ is H.

In an exemplary embodiment of Formula (2), $X_1$ and $X_2$ are each N and each of $R_4$ and $R_5$ is —$NR_6R_6$ where each $R_6$ is H.

In an exemplary embodiment, the compound of Formula (2) is a compound of Formula (2A):

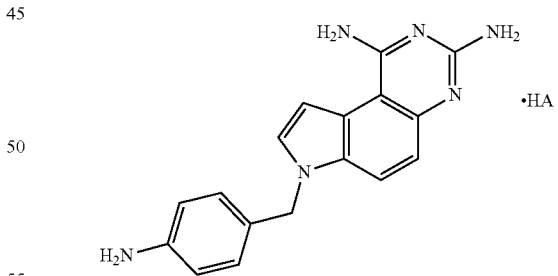

where the compound of Formula (2A) exists as a pharmaceutically acceptable salt, where HA is a proton donor. In an exemplary embodiment, HA is selected from the group consisting of inorganic acids (e.g., hydrochloric acid, hydrobromic acid, sulfuric acid, phosphoric acid, nitric acid, and the like) and organic acids (e.g., acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid and polygalacturonic acid). In a particular embodiment, HA is selected from the group consisting of hydrochloric acid, hydrobromic acid, sulfuric acid, phosphoric acid and nitric acid.

In an exemplary embodiment, the compound of Formula (2) is Compound (2AA):

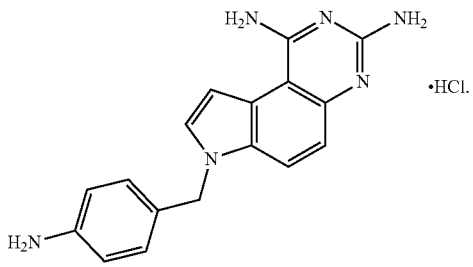 [SMILES: Nc1ccc(Cn2ccc3c4c(N)nc(N)nc4ccc32)cc1 ; "·HCl."]

In an aspect of the invention, the myeloid neoplasm or solid tumor identified for treatment with the compounds disclosed herein is associated with SETBP1 activation (which includes, for example, but is not limited to, activation by overexpression or by mutation). In an exemplary embodiment, the myeloid neoplasm is selected from the group consisting of acute myeloid leukemia (AML), chronic myelomonocytic leukemia (CMML), juvenile myelomonocytic leukemia (JMML), chronic myeloid leukemia blast crisis (CML-BC), atypical chronic myeloid leukemia (aCML), secondary acute myeloid leukemia (sAML), myelodysplastic syndrome (MDS) and chronic neutrophilic leukemia (CNL). In an exemplary embodiment, the solid tumor is selected from the group consisting of breast, colorectal, lung, ovarian, prostate, skin, liver, pancreatic, kidney, endometrium, esophagus, gastric, and head and neck cancers.

In an exemplary embodiment, the compound of Formula (1) is present in a pharmaceutical composition comprising one or more excipients.

In an exemplary embodiment, the compound of Formula (1A) is present in a pharmaceutical composition comprising one or more excipients.

In an exemplary embodiment, the Compound (1AA) is present in a pharmaceutical composition comprising one or more excipients.

In an exemplary embodiment, the compound of Formula (2) is present in a pharmaceutical composition comprising one or more excipients.

In an exemplary embodiment, the compound of Formula (2A) is present in a pharmaceutical composition comprising one or more excipients.

In an exemplary embodiment, the Compound (2AA) is present in a pharmaceutical composition comprising one or more excipients.

Another aspect of the invention is an isolated polypeptide of 240 amino acids comprising the amino acid sequence of SEQ ID NO: 1 which represents polypeptide 25-20 with a 6×His tag. In various exemplary embodiments, the present invention provides for peptides comprising amino acid sequences at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the specified amino acid sequence of SEQ ID NO:1.

In an exemplary embodiment, the isolated polypeptide consists of the amino acid sequence of SEQ ID NO: 1. In various exemplary embodiments, the present invention provides for peptides that consist essentially of, or consist of an amino acid sequence at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the specified amino acid sequence of SEQ ID NO: 1.

In an exemplary embodiment, the isolated polypeptide consists of amino acids 24-240 of SEQ ID NO: 1. In various exemplary embodiments, the present invention provides for peptides that consist essentially of, or consist of an amino acid sequence at least 70%, 71%, 72%, 73%, 74% 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% identical to the specified amino acid sequence of amino acids 24-240 of SEQ ID NO: 1.

Another aspect of the invention is a reagent composition comprising the isolated polypeptide of 240 amino acids comprising the amino acid sequence of SEQ ID NO: 1.

In an exemplary embodiment of the reagent composition, the isolated polypeptide consists of the amino acid sequence of SEQ ID NO: 1.

In an exemplary embodiment of the reagent composition, the isolated polypeptide consists of amino acids 24-240 of SEQ ID NO: 1.

BRIEF DESCRIPTION OF THE DRAWINGS

The following figures are merely illustrative of specific embodiments of the invention and are not intended to otherwise limit the full scope of the invention as described.

In FIG. 5A (upper panels) apoptotic cells were detected by Annexin V staining in Setbp1-immortalized myeloid progenitor cells at 48 hours after treatment with either KPT-185 or DMSO. FIG. 5A (lower panels) shows cytospin analysis of the same cells at 72 hours after the treatments. The number of mature neutrophils was observed to significantly increase in the culture after treatment with KPT-185. FIG. 5B shows the same analyses as in FIG. 5A performed on Setbp1(D/N)-immortalized myeloid progenitors.

Figure 17:
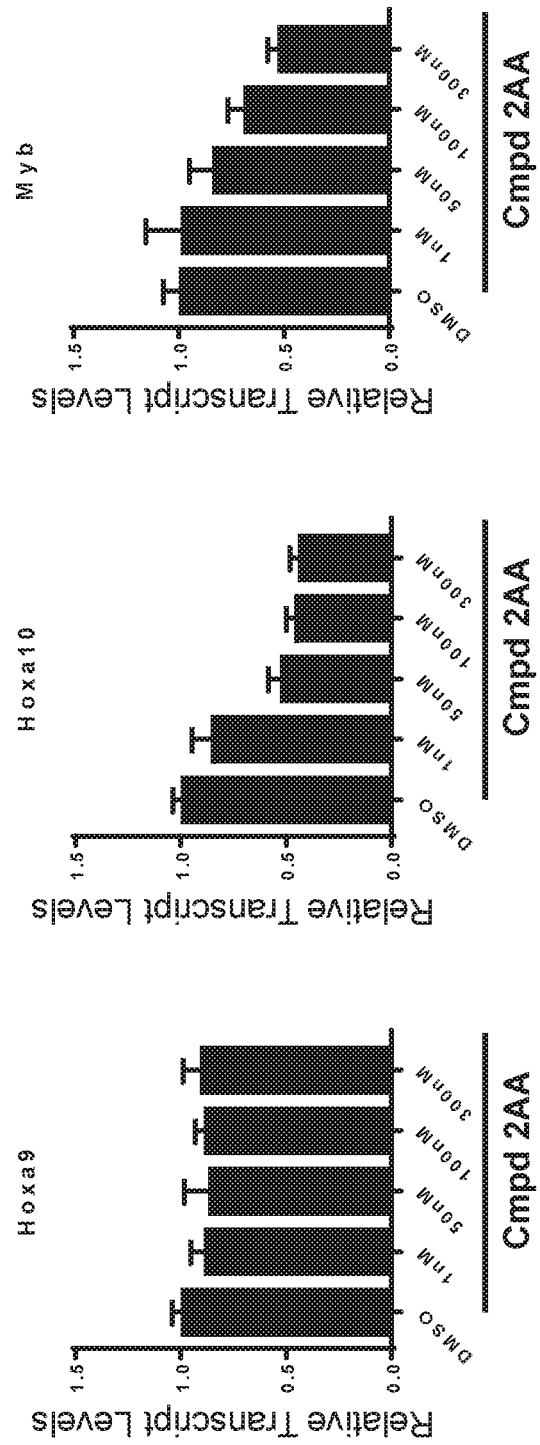

FIG. 17 shows that Compound (2AA) reduces Setbp1 (D/N) target transcription levels of Hoxa9, Hoxa10 and Myb at 12 hours post-treatment at concentrations of 1 nM, 50 nM, 100 nM and 300 nM in Setbp1 (D/N)-immortalized cells.

FIG. 18 shows the polypeptide 25-20 sequence with a 6×His tag that is SEQ ID NO: 1.

Figure 19:
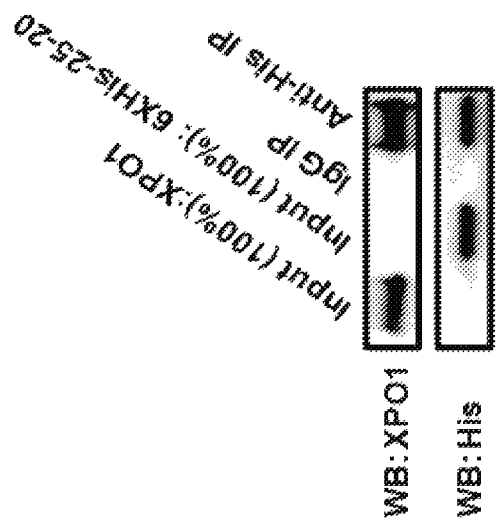

FIG. 19 shows that polypeptide 25-20 interacts with XPO1.

Figure 20:
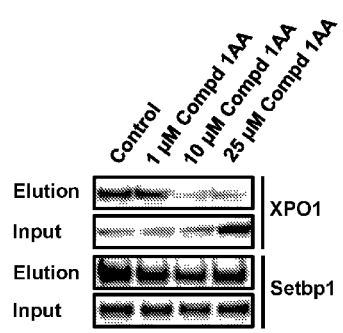

FIG. 20 illustrates that Compound (1AA) disrupts the interaction between Setbp1(D/N) and XPO1 at concentrations of 1 µM, 10 µM and 25 µM. Western blotting analyses using indicated specific antibodies were performed on M2 immunoprecipitates prepared from nuclear extracts of HEK293T cells transiently transfected with pMYs-3× FLAG-Setbp1-IRES-GFP and subsequently treated with different concentrations of Compound (1AA) and control DMSO for 12 hours.

Figure 21:
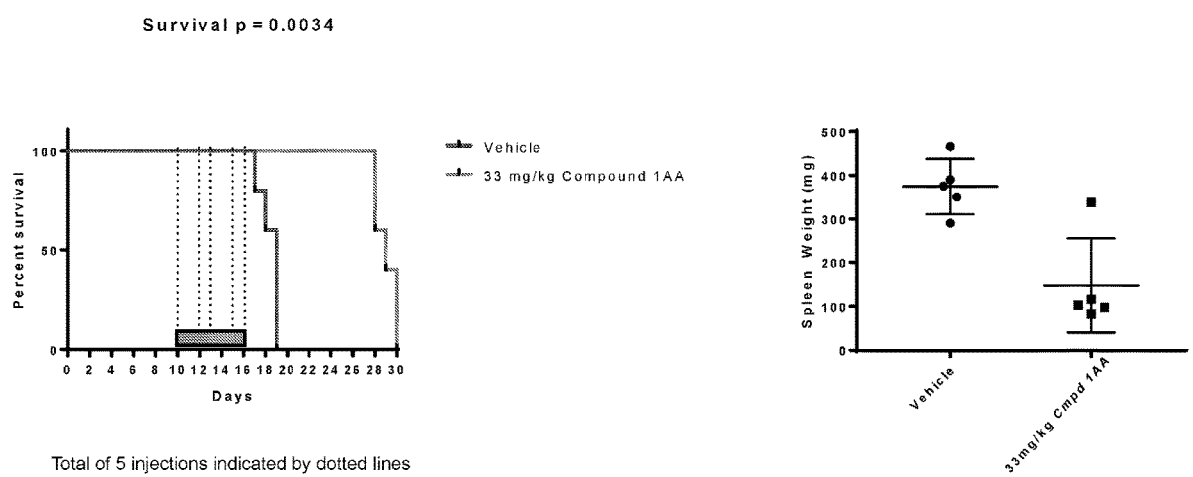

FIG. 21 illustrates that Compound (1AA) significantly extended the survival and reduced the spleen size of leukemic mice transplanted with mouse AML induced by Setbp1 (D/N) and reduced their spleen size. LEFT panel shows survival curves of sublethally irradiated B6-Ly5.2 mice transplanted with a Setbp1(D/N)-induced leukemia and treated with Compound (1AA) (33 mg/kg of body weight) or vehicle. Animals were treated with five intra-peritoneal injections starting from 10 days after transplantation. p=0.0034, Log-rank test. RIGHT panel shows spleen weights of mice in LEFT panel when becoming moribund.

DETAILED DESCRIPTION

Definitions

The term, "pharmaceutically acceptable carrier" as used herein, includes any and all solvents, or a dispersion medium including, but not limited to, water, ethanol, a polyol (for example, glycerol, propylene glycol, and liquid polyethylene glycol, and the like), suitable mixtures thereof, and vegetable oils, coatings, isotonic and absorption delaying agents, liposomes, commercially available cleansers, and the like. Supplementary bioactive ingredients also can be incorporated into such carriers.

The term "alkyl", as used herein, means any straight chain or branched, non-cyclic or cyclic, unsaturated or saturated aliphatic hydrocarbon containing, for example, from 1 to 20 carbon atoms, while the term "lower alkyl" has the same meaning as alkyl but contains from 1 to 5 carbon atoms. The term "higher alkyl" has the same meaning as alkyl but contains from 6 to 20 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as "cycloalkyls", "homocycles" or "homocyclic rings." Unsaturated alkyls contain at least one double or triple bond between adjacent carbon atoms (referred to as an "alkenyl" or "alkynyl", respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl", as used herein, refers to any aromatic carbocyclic moiety containing, for example, 5 to 20 carbon atoms such as, but not limited to, phenyl or naphthyl.

The term "arylalkyl", or "aralkyl" as used herein, refers to any alkyl having at least one alkyl hydrogen atom replaced with an aryl moiety, such as benzyl, but not limited to, —(CH$_2$)$_2$phenyl, —(CH$_2$)$_3$phenyl, —CH(phenyl)$_2$, and the like.

The term "halogen" or "halo" as used herein, refers to any fluoro, chloro, bromo, or iodo moiety.

The term "haloalkyl" as used herein, refers to any alkyl having at least one hydrogen atom replaced with halogen, such as trifluoromethyl, and the like.

The term "heteroaryl" as used herein, refers to any aromatic heterocycle ring of 5 to 20 members and having at least one heteroatom selected from nitrogen, oxygen and sulfur, and containing at least one carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl" as used herein, refers to any alkyl having at least one alkyl hydrogen atom replaced with a heteroaryl moiety, such as —CHpyridinyl, —CH$_2$pyrimidinyl, and the like.

The term "heterocycle" or "heterocyclic", "heterocyclyl" or "heterocyclic ring", as used herein, refers to any non-aromatic 3- to 7-membered monocyclic or any non-aromatic 7- to 10-membered bicyclic heterocyclic ring which is either saturated or unsaturated and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include, but are not limited to, morpholinyl, pyrrolidinonyl, pyrrolidinyl, piperidinyl, piperazinyl, imidazolinyl, imidazolidinyl, pyrazolinyl, pyrazolidinyl, 1,4-dioxanyl, dithianyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl", as used herein, refers to any alkyl having at least one alkyl hydrogen atom replaced with a heterocycle, such as —CH$_2$morpholinyl, and the like.

The term "homocycle" or "cycloalkyl", as used herein, refers to any saturated or unsaturated (non-aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino", as used herein, refers to at least one alkyl moiety attached through a nitrogen bridge (i.e., —N-(alkyl)N, such as a dialkylamino) including, but not limited to, methylamino, ethylamino, dimethylamino, diethylamino, and the like.

The term "alkyloxy" or "alkoxy", as used herein, refers to any alkyl moiety attached through an oxygen bridge (i.e., —O-alkyl) such as, but not limited to, methoxy, ethoxy, and the like.

The term "alkylthio", as used herein, refers to any alkyl moiety attached through a sulfur bridge (i.e., —S— alkyl) such as, but not limited to, methylthio, ethylthio, and the like.

The term "salts" as used herein, refers to any salt that complexes with identified compounds described herein. Examples of such salts include, but are not limited to, acid addition salts formed with inorganic acids (e.g., hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known to a person skilled in the art, which specifically includes the quaternary ammonium salts of the formula —NRR'R"+Z—, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In various exemplary embodiments, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository, etc.

The term "patient", as used herein, is an animal, such as, for example, a mammal, such as, for example, a human that need not be hospitalized. For example, out-patients and persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "subject" as used herein refers to a vertebrate, preferably a mammal, more preferably a primate, still more preferably a human. Mammals include, without limitation, humans, primates, wild animals, feral animals, farm animals, sports animals and pets.

In an exemplary embodiment, the invention provides a pharmaceutical composition comprising at least one pharmaceutically-acceptable carrier, in addition to one or more of the compounds described herein. The composition can be present in any suitable form for the desired route of administration. Where the composition is to be administered orally, any suitable orally deliverable dosage form can be used, including, without limitation, tablets, capsules (solid or liquid filled), powders, granules, syrups and other liquids, elixirs, inhalants, troches, lozenges and solutions. Injectable compositions or i.v. infusions are also provided in the form of solutions, suspensions, and emulsions.

The compounds of the invention can be formulated as described herein and are suitable for administration in a therapeutically effective amount to the subject in any number of ways. A therapeutically effective amount of a compound as described herein depends upon the amounts and types of excipients employed, the amounts and specific types of active ingredients present in a dosage form, and the route by which the compound is to be administered to patients.

Typical dosage levels for the compounds of the invention generally range from about 0.001 to about 100 mg per kg of the subject's body weight per day which can be administered in single or multiple doses. An exemplary dosage is about 0.01 to about 25 mg/kg per day or about 0.05 to about 10 mg/kg per day. In other exemplary embodiments, the dosage level ranges from about 0.01 to about 25 mg/kg per day, such as about 0.05 to about 10 mg/kg per day, or about 0.1 to about 5 mg/kg per day.

A dose can typically range from about 0.1 mg to about 2000 mg per day and can be given as a single once-a-day dose or, alternatively, as divided doses throughout the day, optionally taken with food. In a particular embodiment, the daily dose is administered twice daily in equally divided doses. A daily dose range can range from about 5 mg to about 500 mg per day such as, for example, between about 10 mg and about 300 mg per day. In managing the patient, the therapy can be initiated at a lower dose, such as from about 1 mg to about 25 mg, and increased if necessary up to from about 200 mg to about 2000 mg per day as either a single dose or divided doses, depending on the subject's global response.

Suitable oral compositions in accordance with the invention include, without limitation, tablets, troches, lozenges, aqueous or oily suspensions, dispersible powders or granules, emulsion, hard or soft capsules, syrups or elixirs. Inventive compositions suitable for oral use may be prepared according to any method known to the art for the manufacture of pharmaceutical compositions. For example, liquid formulations of the compounds can contain one or more agents selected from the group consisting of sweetening agents, flavoring agents, coloring agents and preserving agents in order to provide pharmaceutically elegant and palatable preparations of the active agents.

For tablet compositions, typical non-toxic pharmaceutically acceptable excipients include, without limitation, inert diluents such as calcium carbonate, sodium carbonate, lactose, calcium phosphate or sodium phosphate; granulating and disintegrating agents such as, for example, corn starch, or alginic acid; binding agents such as, for example, starch, gelatin or lubricating agents such as, for example, magnesium stearate, stearic acid or talc. The tablets may be uncoated or, alternatively, they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent such as, for example, calcium carbonate, calcium phosphate or kaolin, or as soft gelatin capsules wherein the active ingredient is mixed with water or an oil medium such as, for example peanut oil, liquid paraffin or olive oil.

For aqueous suspensions, the compound is admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide such as, for example, lecithin, or condensation products of an alkylene oxide with fatty acids such as, for example, polyoxyethylene stearate, or condensation products of ethylene oxide with long chain aliphatic alcohols such as, for example, heptadecaethyleneoxycetanol, or condensation products of ethylene oxide with partial esters derived from fatty acids and a hexitol such as, for example, polyoxyethylene sorbitol monooleate, or condensation products of ethylene oxide with partial esters derived from fatty acids and hexitol anhydrides such as, for example, polyethylene sorbitan monooleate. The aqueous suspensions may also contain one or more preservatives such as, for example, ethyl or n-propyl p-hydroxybenzoate, one or more coloring agents, one or more flavoring agents, and one or more sweetening agents such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients such as, for example, sweetening, flavoring and coloring agents, may also be present.

Syrups and elixirs may be formulated with sweetening agents such as, for example, glycerol, propylene glycol, sorbitol or sucrose. Such formulations may also contain a demulcent, a preservative, and flavoring and coloring agents.

Compositions for parenteral administrations are formulated in a sterile medium suitable for intravenous, intramuscular or intrathecal delivery. A sterile injectable preparation of the compounds may be in the form of a sterile injectable solution or sterile injectable suspension. Non-toxic, parentally acceptable diluents or solvents such as, for example, 1,3-butanediol can be used to formulate the parenteral compositions. Among the acceptable vehicles and solvents that may be employed are water, Ringer's solution and isotonic sodium chloride solution. In addition, sterile oils also can be employed as a solvent or a suspending medium. For this purpose, any bland fixed oil may be employed, including synthetic monoglycerides or diglycerides. In addition, fatty acids such as oleic acid can be used in the preparation of injectables.

Depending on the vehicle used and the concentration of the drug in the formulation, the parenteral formulation can contain other adjuvants such as local anesthetics, preservatives and buffering agents.

The pharmaceutical compositions according to the invention may contain one or more additional therapeutic agents, for example, to increase efficacy and/or to decrease side effects. Examples of such agents include, without limitation, agents to treat or inhibit immunological, inflammatory, autoimmune or allergic disorders.

SETBP1 and XPO1

Figure 1:
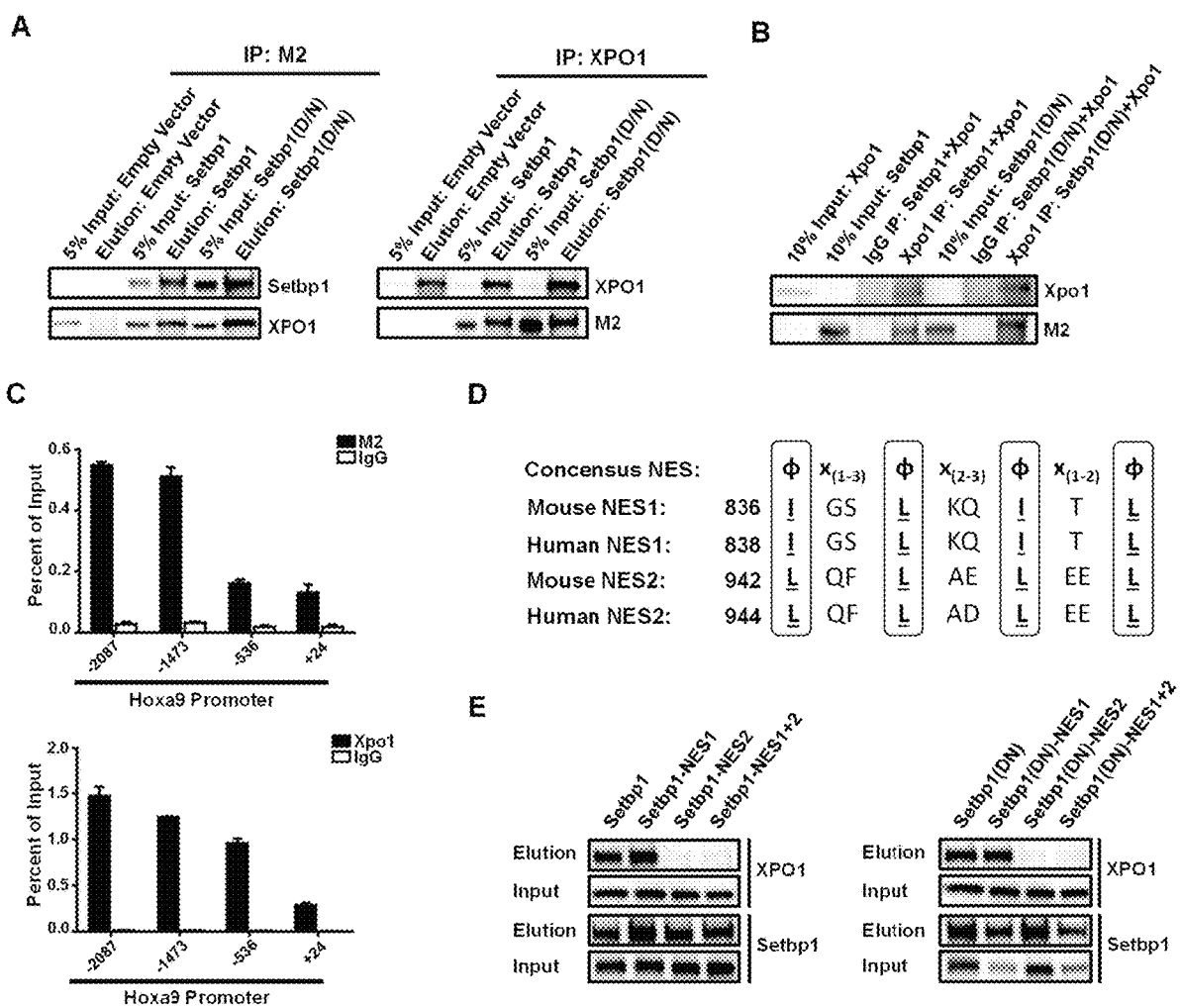
FIG. 1A illustrates complex formation by Setbp1/Setbp1 (D/N) and XPO1 in HEK293T cells. The LEFT panel shows Western blotting analyses of M2 immunoprecipitates prepared from a nuclear extract of HEK293T cells transiently transfected with pMYs-3×FLAG-Setbp1-IRES-GFP, pMYs-3×FLAG-Setbp1(D/N)-IRES-GFP or control empty vector pMYs-IRES-GFP using the indicated specific antibodies. The RIGHT panel shows Western blotting analyses of immunoprecipitates prepared using a XPO1-specific antibody from HEK293T cells similarly transfected as in the LEFT panel. Setbp1 (D/N) is a Setbp1 mutant carrying a missense mutation identified frequently in patients of myeloid neoplasms.
FIG. 1B illustrates direct physical interaction between Setbp1/Setbp1(D/N) and Xpo1. Western blotting analyses were performed on immunoprecipitates prepared from mixture of Xpo1 protein with 3×FLAG-tagged Setbp1 or Setbp1 (D/N) protein using indicated antibodies. Xpo1, Setbp1 and Setbp1(D/N) proteins were produced by in vitro transcription and translation. Immunoprecipitation was performed using an Xpo1-specific antibody or control IgG.
FIG. 1C illustrates direct binding of Setbp1 to Hoxa9 locus. Chromatin immunoprecipitation (ChIP) analyses of indicated regions of Hoxa9 locus relative to the transcriptional start site using an anti-Xpo1 or M2 antibody in 3×FLAG-tagged Setbp1-immortalized myeloid progenitor cells were performed and analyzed by quantitative real-time PCR.
FIG. 1D illustrates alignment of mouse and human Setbp1 NES1 and NES2 sequences to the NES consensus sequence. "Φ" indicates a hydrophobic residue while "X" represents any other amino acid.
FIG. 1E illustrates that NES2 is responsible for mediating the interaction between Setbp1/Setbp1(D/N) and Xpo1. The LEFT panel shows Western blotting analyses of M2 immunoprecipitates prepared from a nuclear extract of HEK293T cells transiently transfected with a pMYs retroviral construct expressing 3xFLAG-tagged wild-type Setbp1 or Setbp1 NES mutants using the indicated specific antibodies. The RIGHT panel represents Western blotting analyses of M2 immunoprecipitates prepared from a nuclear extract of HEK293T cells transiently transfected with a pMYs construct expressing 3xFLAG-tagged Setbp1(D/N) or Setbp1 (D/N) NES mutants using indicated specific antibodies.

Setbp1 and XPO1 were observed to physically associate with each other in HEK293T cells. It was previously shown that Setbp1 is a transcriptional regulator capable of activating oncogenes Hoxa9 and Hoxa10 and such activations are likely essential for Setbp1 activation induced transformation of myeloid progenitors (Oakley et al., Blood 119(25):6099-6108 (2012)). In an effort to identify potential co-factors critically involved in SETBP1-mediated transcriptional regulation, the inventors have found that XPO1 can be efficiently immunoprecipitated using the FLAG tag specific M2 antibody from nuclear extracts of HEK293T cells transfected with a DNA construct expressing 3×FLAG-tagged wild-type Setbp1. Similarly, XPO1 can also be pulled down by Setbp1(D/N), a Setbp1 mutant with a recurrent missense mutation (D868N) identified in human leukemia patients (FIG. 1A). In addition, both FLAG-tagged Setbp1 proteins could also be efficiently immunoprecipitated with a XPO1-specific antibody from these nuclear extracts (FIG. 1A). These results suggest that XPO1 can associate with both Setbp1 and Setbp1(D/N) in complex formation.

To test whether Setbp1 and Xpo1 can interact directly with each other, the cDNAs for Setbp1, Setbp1(D/N), and Xpo1 were cloned into pCMV-TNT vector and the proteins were synthesized through in vitro transcription and translation using wheat germ extract. The synthesized Setbp1 proteins were subsequently incubated with Xpo1 protein individually to examine potential direct interaction by co-immunoprecipitation (FIG. 1B). A significant amount of both Setbp1 and Setbp1(D/N) was observed to be pulled down together with Xpo1 by a Xpo1-specific antibody, strongly suggesting that both Setbp1 and Setbp1(D/N) directly interact with Xpo1 (FIG. 1B).

The physical interaction of Xpo1 with Setbp1 and Setbp1 (D/N) suggested that Xpo1 was a co-factor for both to regulate transcription by binding to chromatin (Conway et al., Leukemia 29(2): 423-432 (2015); and Oka et al., Elife 5: e09540 (2016). This possibility was tested by chromatin immunoprecipitation (ChIP) assays in myeloid progenitor cells immortalized by the expression of 3×FLAG-tagged Setbp1 using an Xpo1 specific antibody. Regions of the Hoxa9 promoter were readily detected in the precipitates prepared by the Xpo1 antibody, similar to the precipitates generated by FLAG M2 antibody (FIG. 1C), supporting the idea that Xpo1 cooperates with Setbp1 and Setbp1(D/N) to directly regulate the transcription of Setbp1 target genes.

Figure 2:
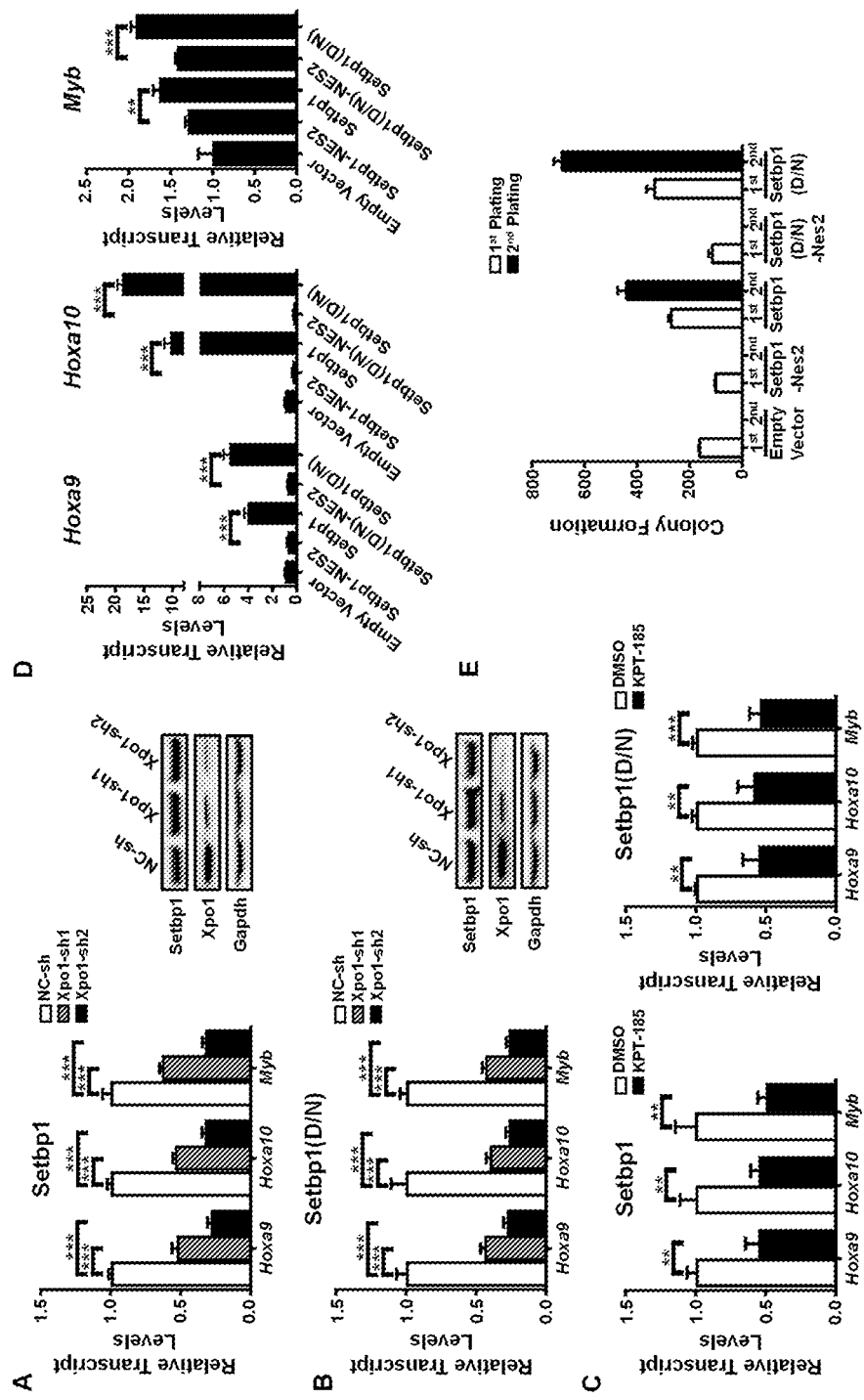
FIG. 2A illustrates that Xpo1 is required for Setbp1 to induce transcriptional activation. The LEFT panel represents real-time RT-PCR analysis of Hoxa9, Hoxa10 and Myb mRNA levels in mouse myeloid progenitor cells immortalized by wild-type Setbp1 at 54 hours after infection with lentiviral shRNAs targeting Xpo1 (Xpo1-sh1 and -sh2) or non-targeting control lentiviral shRNA (NC-sh). Relative expression levels were calculated by normalizing to β-Actin mRNA levels in the same sample and also to cells infected with NC-sh virus. The mean and SD of each relative expression level is shown. The RIGHT panel represents Western blotting analyses of the same transduced cells in the LEFT panel using the indicated antibodies. ***, $P<0.001$ (two-tailed Student's t test)
FIG. 2B illustrates that Xpo1 is required for Setbp1(D/N) to induce transcriptional activation. The same analyses as in FIG. 2A were performed on Setbp1(D/N)-immortalized mouse myeloid progenitors.
FIG. 2C illustrates inhibition of Setbp1/Setbp1(D/N)-induced transcriptional activation by XPO1 inhibitor KPT-185. Hoxa9, Hoxa10, and Myb mRNA levels in mouse myeloid progenitor cells immortalized by Setbp1 (LEFT panel) and Setbp1(D/N) (RIGHT panel) were analyzed by real-time RT-PCR at 2.5 hours after treatment with KPT-185 (300 nM) or DMSO as a control. , $P<0.01$; *, $P<0.001$ (two-tailed Student's t test).
FIG. 2D illustrates that NES2 mutations in Setbp1 and Setbp1(D/N) inhibit their capability to induce transcriptional activation in normal hematopoietic stem and progenitor cells. Hoxa9, Hoxa10, and Myb mRNA levels in mouse LSK cells at 72 hours after infection with the indicated pMYs retrovirus were analyzed by real-time RT-PCR. Transduced cells were purified based on GFP positivity. , $P<0.01$; *, $P<0.001$ (two-tailed Student's t test).
FIG. 2E illustrates that NES2 mutations in Setbp1 and Setbp1(D/N) inhibit their capability to induce self-renewal of normal hematopoietic stem and progenitor cells. Serial replating assays were performed on the same mouse LSK cells as in FIG. 2D. The mean and SD of colony numbers formed by $5\times10^3$ transduced LSK cells on IMDM methylcellulose medium in the presence of mouse Scf (100 ng/ml), Il-6 (10 ng/ml), and Il-3 (6 ng/ml) are shown. Five days after the 1st plating, colonies were counted and same number of colony cells were used for the 2nd plating under the same condition.
Figure 3:
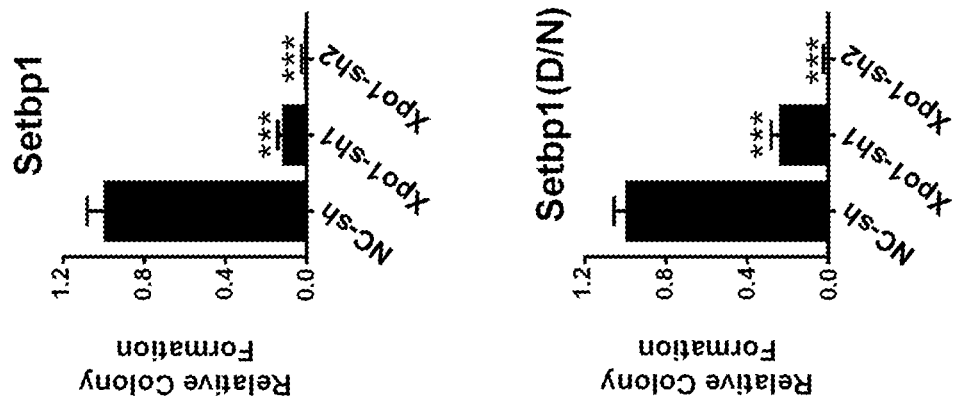
FIG. 3 shows that Xpo1 knockdowns significantly decrease colony-forming potential of myeloid progenitors immortalized by Setbp1 and Setbp1(D/N). Mean and SD of relative colony-forming potential of Setbp1 or Setbp1(D/N)-immortalized myeloid progenitors transduced with lentiviral shRNAs targeting Xpo1 (Xpo1-sh1 and Xpo1-sh2) or control shRNA (NC-sh) on methylcellulose in the presence of murine Scf (50 ng/ml) and Il-3 (10 ng/ml).

To determine whether XPO1 is important for SETBP1 and SETBP1(D/N) to activate target gene transcription, Xpo1 expression was knocked down in myeloid progenitors immortalized by Setbp1 or Setbp1(D/N) using two different lentiviral shRNAs and the mRNA levels of Setbp1 target genes Hoxa9, Hoxa10 and Myb were examined at 54 hours after transduction. Xpo1 knockdown by lentiviral shRNAs in these cells were observed to cause significant reductions in Hoxa9, Hoxa10 and Myb mRNA levels and their colony-forming potentials (FIGS. 2A and 2B and FIG. 3). These results strongly suggest that XPO1 is an essential co-factor for Setbp1 to activate its target gene transcription.

Figure 7:
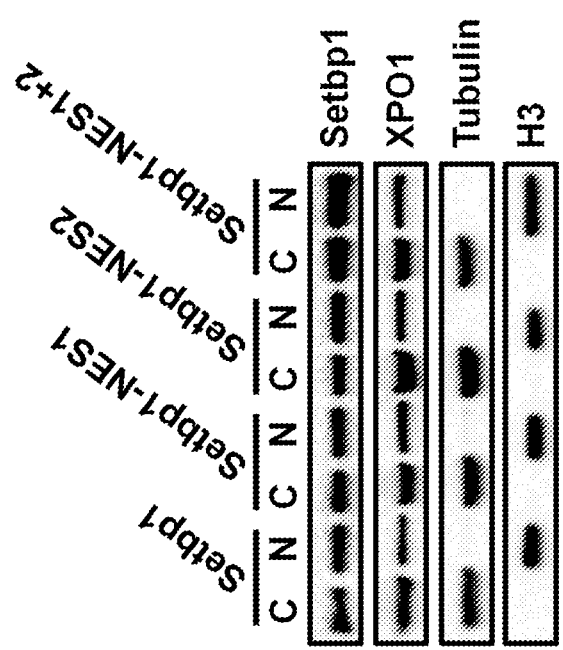
FIG. 7 shows that cellular localization of SETBP1 and XPO1 in HEK293T cells is not affected by NES mutations. Western blotting analyses of nuclear and cytoplasmic fractions of HEK293T cells transiently expressing indicated 3xFLAG-tagged Setbp1 or Setbp1 mutants with specified NES mutations using indicated antibodies.

Xpo1 is known to interact with its cargo proteins through their nuclear exportation signals (NESs), which have a consensus of $\Phi XXX\Phi XX\Phi X\Phi$, where $\Phi$ is a hydrophobic residue (often leucine and isoleucine) and X is any other amino acid (Kosugi et al., Traffic 9(12): 2053-2062 (2008). Two potential NESs were identified in SETBP1 based on sequence similarity to the consensus sequence (FIG. 1D). To determine whether the NESs were responsible for mediating the interaction with Xpo1, each NESs was subsequently mutated in Setbp1 and Setbp1(D/N) separately or together by replacing their leucine and isoleucine residues with alanine residues, and the capability of the mutant proteins to interact with XPO1 in HEK293T cells by immunoprecipitation was tested (FIG. 1E). Similar cellular distribution patterns were observed between Setbp1 and its NES mutants, suggesting that NES mutations do not significantly affect the cellular localization of Setbp1 (FIG. 7). Similar to Setbp1 and Setbp1(D/N), both NES1 single mutants—Setbp1-NES1 and Setbp1(D/N)-NES1)—were competent for binding with XPO1 (FIG. 1E), suggesting that NES1 is not required for the interaction with XPO1. In contrast, both NES2 single mutants—(Setbp1-NES2 and Setbp1(D/N)-NES2)—as well as the NES1 and NES2 double mutants—(Setbp1-NES1+2 and Setbp1(D/N)-NES1+2)—completely lost the ability to interact with XPO1 (FIG. 1E), further evidence that the interaction between Setbp1/Setbp1(D/N) and Xpo1 is mediated by NES2.

Figure 4:
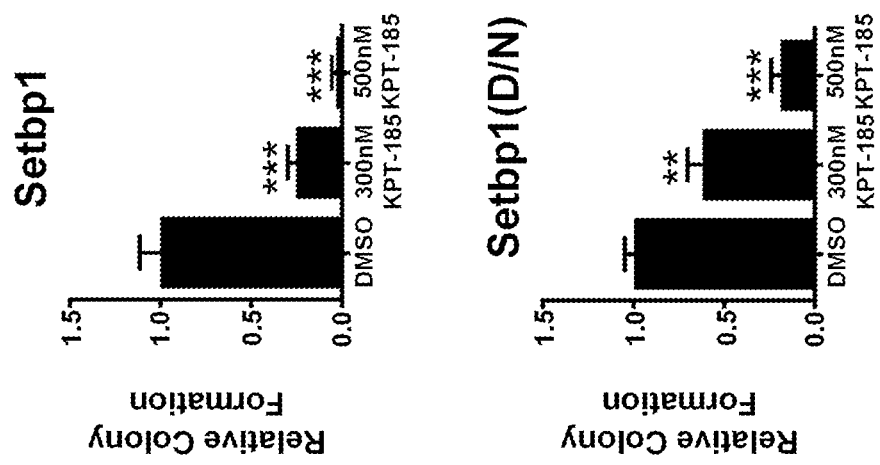
FIG. 4 shows that KPT-185 significantly reduces colony-forming potential of myeloid progenitors immortalized by Setbp1 activation. Mean and SD of relative colony-forming potential of Setbp1 or Setbp1(D/N)-immortalized myeloid progenitors treated with the indicated concentrations of KPT-185 or control DMSO on methylcellulose in the presence of murine Scf (50 ng/ml) and Il-3 (10 ng/ml).
Figure 5:
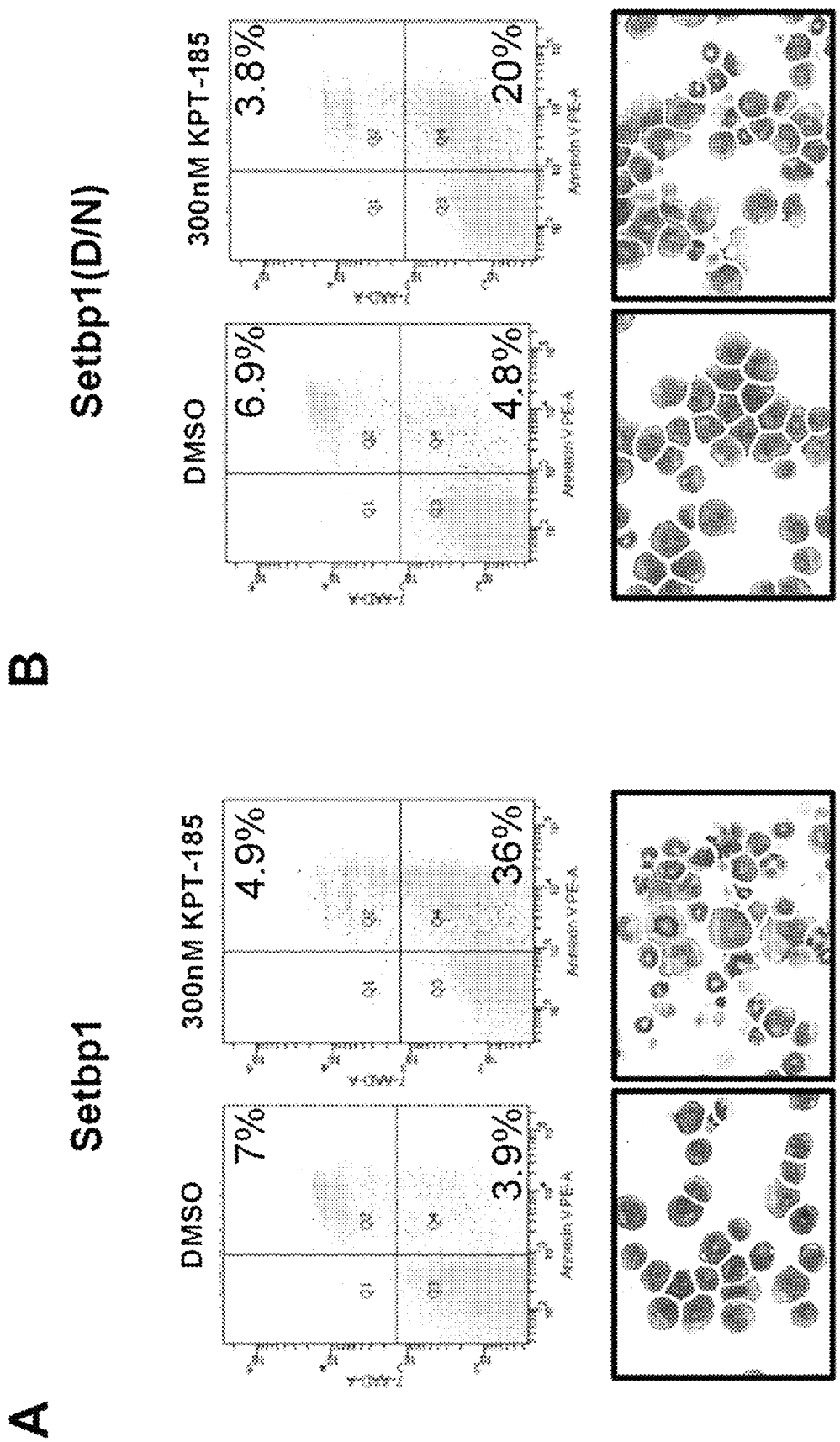
FIG. 5A and FIG. 5B show that treatment with KPT-185 induces apoptosis and differentiation in myeloid progenitors immortalized by Setbp1 and Setbp1(D/N).
Figure 6:
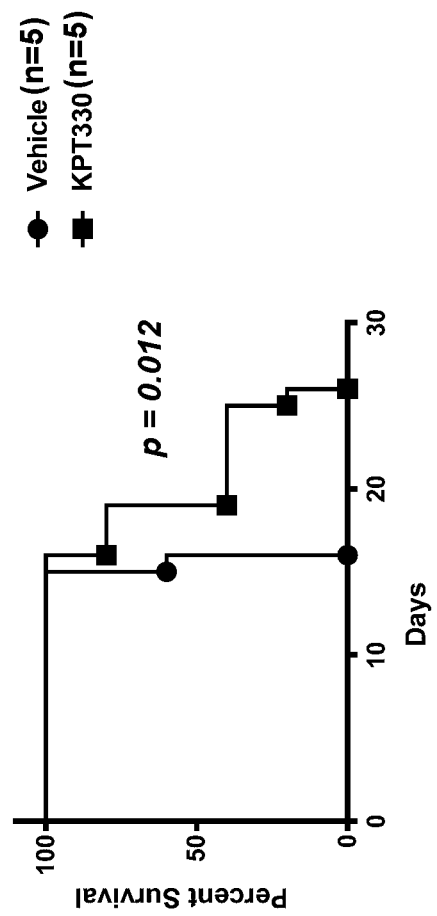
FIG. 6 shows that treatment with XPO1 inhibitor KPT-330 prolonged the survival of mice transplanted with mouse AML induced by Setbp1(D/N). Survival curves of irradiated B6-Ly5.2 mice transplanted with a Setbp1(D/N)-induced leukemia and treated with KPT-330 (20 mg/kg of body weight) or vehicle. Animals were treated by oral gavage every 2 days starting from 7 days after transplantation. $p=0.012$, Log-rank test.

The NES-mediated interaction between Setbp1/Setbp1 (D/N) and Xpo1 suggests that it should be blocked by XPO1 inhibitors. To test this idea, the effects of KPT-185 (a selective XPO1 inhibitor) on Hoxa9/Hoxa10/Myb transcription in myeloid progenitors immortalized by Setbp1 and Setbp1(D/N) were tested. The Hoxa9/Hoxa10/Myb mRNA levels were observed to be significantly down-regulated in the immortalized cells as early as 2.5 hours after treatment with KPT-185 (FIG. 2C). Treatment with KPT-185 was also observed to significantly inhibit colony formation by these cells (FIG. 4), which was likely due to increased apoptosis and induction of differentiation in treated cells (FIG. 5). To test the potential efficacy of XPO1 inhibition in treating leukemias with SETBP1 activation in vivo, mice with a primary mouse AML induced by Setbp1(D/N) were transplanted and the recipient mice were treated with KPT-330 (a selective inhibitor of XPO1 also known as Selinexor) or a vehicle once every two days starting from 7 days post transplantation (FIG. 6). All recipient mice treated with vehicle became moribund due to leukemia development in 17 days. In contrast, KPT-330 treatments were observed to significantly prolong the survival of all leukemic mice with up to a 50% extension of their survival time. Collectively, these results suggest that interaction with Xpo1 is critical for Setbp1 and Setbp1(D/N) to activate Hoxa9/Hoxa10/Myb transcription. As a result, XPO1 inhibition may represent a promising therapeutic strategy for treating myeloid neoplasms with SETBP1 activation.

Figure 8:
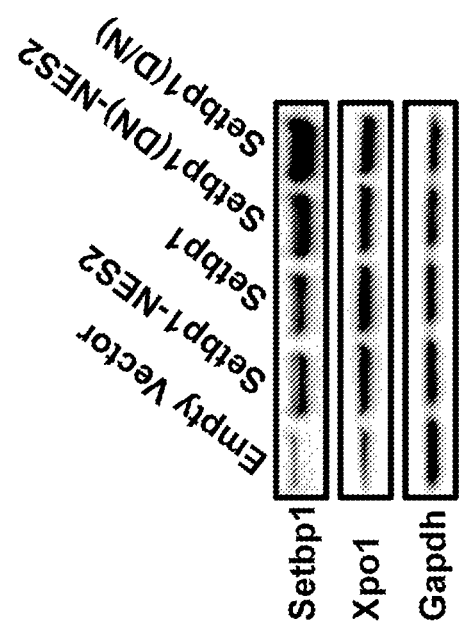
FIG. 8 shows Western blotting analyses of mouse LSK cells at 72 hours after infection with the indicated pMYs retrovirus using indicated antibodies.
Figure 9:
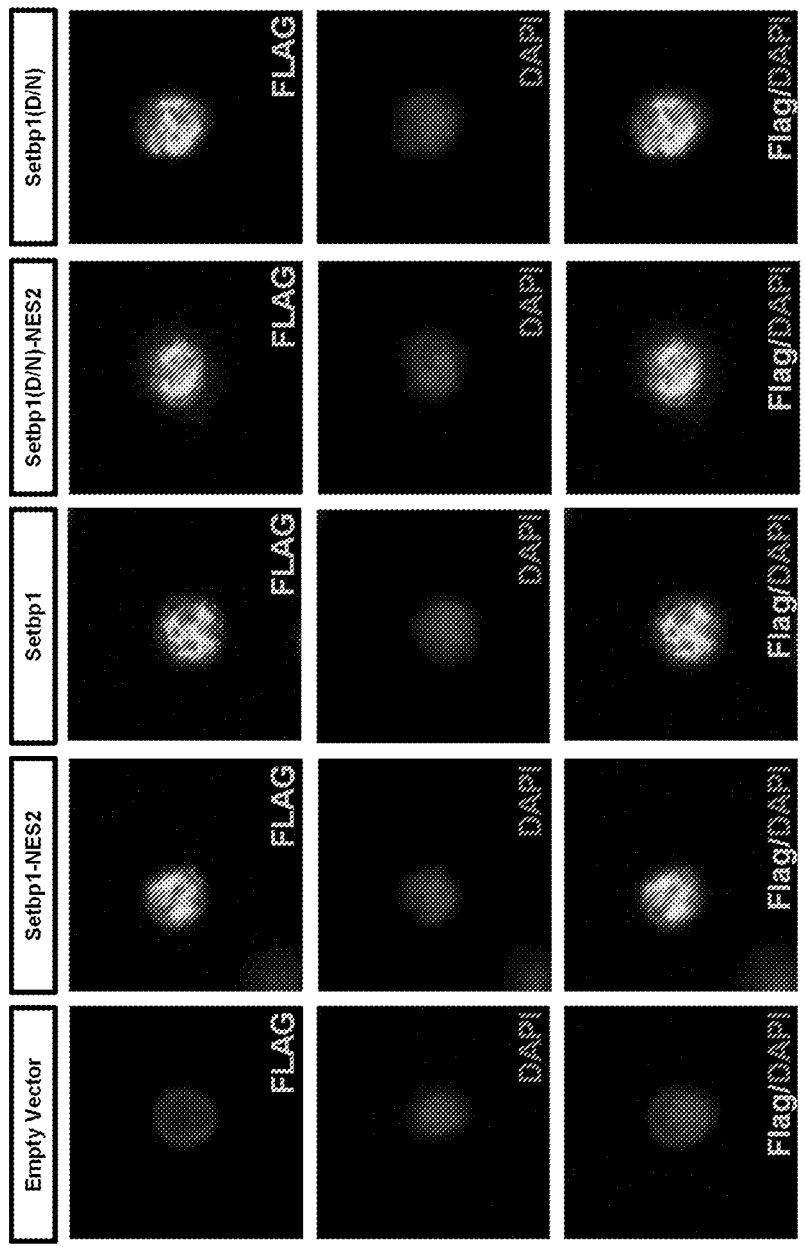
FIG. 9 shows that NES2 mutation does not affect nuclear localization of Setbp1 and Setbp1(D/N) proteins in mouse LSK cells. Detection of 3xFLAG-tagged Setbp1-NES2, Setbp1, Setbp1(D/N)-NES2, or Setbp1(D/N) protein by immunofluorescence using anti-FLAG M2 antibody in mouse LSK cells at 72 hours after infection with corresponding pMYs retroviral expression constructs. Nuclei were marked by staining with DAPI. LSK cells transduced with empty virus (pMYs-IRES-GFP) were included as a negative control.

The oncogenic potentials of SETBP1 and its missense mutants are likely dependent on their capability to induce self-renewal of myeloid progenitors. To further test the idea that Xpo1 is a critical cofactor in order for Setbp1 to activate target gene transcription and to induce myeloid transformation in the absence of global inhibition of nuclear exportation potentially induced by Xpo1 knockdown or treatment with KPT-185, the ability of Setbp1-NES2 and Setbp1(D/N)-NES2 to induce serial replating activity of purified mouse lin-Sca-1+c-kit+(LSK) cells, which were enriched for hematopoietic stem and progenitor cells, was evaluated in comparison to their wild-type counterparts. The LSK cells transduced by retrovirus expressing either Setbp1-NES2 or Setbp1 (D/N)-NES2 were observed not to express significantly higher levels of Hoxa9/Hoxa10/Myb mRNAs than cells transduced by empty virus at 72 hours after transduction (FIG. 2D), even though the mutant proteins were detected at similar levels to their wild-type counterparts and were also present in the nucleus of the transduced cells (FIGS. 8 and 9). In contrast, consistent with their inability to activate Hoxa9/Hoxa10/Myb transcription, cells expressing Setbp1-NES2 or Setbp1(D/N)-NES2 also failed to form any colonies in the secondary plating (FIG. 2E). These results suggest that interaction with Xpo1 through NES2 is essential for Setbp1 and its missense mutants to induce transcriptional activation and leukemic transformation.

Setbp1/Setbp1(D/N)-mediated transcriptional activation is essential for Setbp1/Setbp1(D/N)-induced transformation and its inhibition represents a viable strategy for treating myeloid neoplasms with SETBP1 activation which are associated with a poor prognosis. However, the molecular mechanism responsible for this transcriptional activation in myeloid progenitors is not currently known. As described herein, Xpo1 appears to be a critical cofactor for Setbp1/Setbp1(D/N) to activate transcription. This idea is supported by direct physical interaction between Xpo1 and Setbp1/Setbp1(D/N) and their co-localization at the Hoxa9 promoter in Setbp1-immortalized cells. In addition, disrupting this interaction either by Xpo1 knockdown or treatment with XPO1 inhibitors was observed to result in rapid reductions in mRNA levels of Setbp1/Setbp1(D/N) targets, including Hoxa9, Hoxa10, and Myb. These reductions are not likely secondary effects of inhibiting nuclear exportation of Xpo1 cargo molecules since mutant Setbp1/Setbp1(D/N) proteins incapable of interacting with Xpo1 also failed to induce Hoxa9/Hoxa10/Myb transcription and subsequent immortalization of myeloid progenitors.

Experimental

As an approach to identify small molecules capable of blocking the interaction between SETBP1 and XPO1 without inhibiting the normal function of XPO1, compounds capable of interacting with the Setbp1 regions surrounding NES2 were screened. It was discovered that by co-immunoprecipitation, a bacterially synthesized fragment of Setbp1 protein (polypeptide 25-20) (FIG. 18), which spanned from a.a. 805 to a.a. 1020 of Setbp1 protein and which contained NES2, was capable of forming a stable interaction with full-length XPO1 (FIG. 19). To identify small molecules that may interact with polypeptide 25-20, compound libraries were screened using the surface plasmon resonance (SPR) based Biacore system through contract with the Biacore Molecular Interaction Shared Resource at Georgetown University. For this screen, His-tagged polypeptide 25-20 was synthesized in bacteria, purified, and immobilized onto a CM5 chip surface using an anti-His tag antibody, and the affinities of compounds to polypeptide 25-20 were measured as they flowed through the chip surface. As controls, interactions of these compounds with His-tagged human serum albumin (HSA) were also similarly assessed. Two compound libraries were initially screened, the Prestwick library containing over 1,200 mostly approved drugs and the NCI Developmental Therapeutics Program (DTP) library with over 2,500 compounds. A total of 77 compounds were found to bind to polypeptide 25-20 with at least 50-fold higher affinities than to HSA in this screen. Some compounds were found to significantly inhibit the growth of mouse myeloid progenitors immortalized by Setbp1 at a 1 uM concentration or less.

Protocols

In Vitro and In Vivo Testing of Compound (1AA). The activity of Compound 1AA against myeloid neoplasms was first determined in vitro by assessing its inhibitory effect on the colony formation by Setbp1/Setbp1(D/N)-immortalized mouse myeloid progenitors on IMDM methylcellulose medium with 20% horse serum plus mouse Scf (50 ng/ml) and Il-3 (10 ng/ml). The in vivo activity of Compound 1AA was evaluated by assessing its capability to reduce spleen size and to extend the survival of mice transplanted with Setbp1(D/N)-induced leukemia cells. For the generation of leukemic mice, $5\times10^5$ spleen cells from a primary recipient mouse with Setbp1(D/N)-induced leukemia were injected into the tail vein of each sublethally irradiated (550 rads from a $^{137}$Cs source) B6-Ly5.2 female mouse. Starting from day 10 after transplantation, the recipient mice were treated with Compound (1AA) (33 mg/kg, dissolved in saline) or saline through five intra-peritoneal injections. The activity of Compound 1AA against solid tumors is determined by assessing its growth inhibitory effects on different human solid tumor cell lines in culture. Specifically, cellular ATP levels of liquid cultures of these cell lines are measured at 72 hours after treatment with serially diluted concentrations of Compound 1AA and compared to untreated cells.

Tested Mice. C57BL/6 and B6-Ly5.2 female mice (7-12 weeks old; Charles River Laboratories, Wilmington, MA) were maintained in the animal facility of Center for Laboratory of Animal Medicine at Uniformed Services University of the Health Sciences (USUHS, Bethesda, MD). All mouse experiments were carried out according to protocols approved by the USUHS Institutional Animal Care and Use Committee.

Retroviral Constructs and Generation of Retroviruses. The pMYs retroviral constructs expressing 3×FLAG-tagged Setbp1 and Setbp1(D/N) proteins (pMYs-3×FLAG-Setbp1-IRES-GFP and pMYs-3×FLAG-Setbp1(D/N)-IRES-GFP) were described previously (Makishima et al., Nature Genetics 45(8): 942-946 (2013); Nguyen et al., Oncotarget 7(52): 86300-86312 (2016)). NES1 and NES2 mutations were generated using QuickChange II site-directed mutagenesis kit (Agilent Technologies, Santa Clara, CA) and the mutant cDNAs were also cloned into pMYs-IRES-GFP vector. High titer retroviruses were produced by transient transfection of Plat-E cells using Fugene-6 (Roche, Indianapolis, IN). Viral titer was assessed by serial dilution and infection of NIH-3T3 cells. For the generation of lentivirus, pLKO.1 lentiviral constructs were purchased from Sigma Aldrich (NC-sh, SHC002; Xpo1-sh1, TRCN0000126578; Xpo1-sh2, TRCN0000151579). Infectious lentiviruses were generated as described previously (Oakley et al., Blood 119(25): 6099-6108 (2012).

Immunoprecipitation. HEK293T cells were transfected with the indicated expression constructs using LipoD293 (SignaGen Laboratories, Rockville, MD) and nuclear extracts were isolated 48 hours after transfection using the Nuclear Complex Co-IP kit (Active Motif, Carlsbad, CA). Nuclear lysates were incubated with either 4 μg of anti-Flag M2 (Sigma Aldrich, St. Louis, MO) or anti-XPO1 (NB100-79802, Novus Biological, Centennial, CO) for 4 hours at 4° C. Subsequently, Dynabeads protein A (Invitrogen, Carlsbad, CA) were added to the nuclear lysate/antibody mixture and incubated for an additional 2 hours at 4° C. Immunoprecipitated proteins were eluted and analyzed by Western blotting analysis. For immunoprecipitation experiments using in vitro transcribed and translated proteins, the corresponding cDNAs were cloned into pCMV-TNT and the TnT T7 Coupled Wheat Germ Extract (Promega, Madison, WI) system was used according to the manufacturer's instructions.

Cell Culture Studies of Immortalized Myeloid Progenitors. Mouse myeloid progenitors immortalized by 3×FLAG-tagged Setbp1 and Setbp1(D/N) were generated and maintained as previously described using pMYs-3×FLAG-Setbp1-IRES-GFP and pMYs-3×FLAG-Setbp1(D/N)-IRES-GFP viruses respectively (Oakley et al., Blood 119 (25): 6099-6108 (2012). Lentiviral transduction of these immortalized cells was carried out by spinoculation in which a mixture of lentivirus and target cells was spun at 2000×g for 90 minutes at 37° C. Transduced cells were selected by treatment with puromycin (2 μg/ml) for 24 hours at 24 hours after lentiviral transduction. Colony formation assays for transduced cells were performed at 48 hours after infection using $1\times10^4$ puromycin-resistant cells on IMDM methylcellulose medium supplemented with 20% horse serum, mouse Scf (100 ng/ml) and Il-3 (10 ng/ml), and puromycin (2 μg/ml) with colony numbers counted after 7 days. For studying effects of KPT-185 (Selleck Chemicals, Houston, TX) in liquid culture, immortalized cells were treated at $2.5\times10^5$ cells/ml concentration. Detection of apoptosis was performed using PE Annexin V Apoptosis Detection Kit (BD Biosciences). KPT-185 was directly added to methylcellulose medium for assessing its effects on colony formation by immortalized cells.

Bone Marrow Transplantation and In Vivo Treatment with KPT-330. For generation of leukemic mice, $1\times10^6$ spleen cells from a primary recipient mouse with Setbp1(D/N)-induced leukemia were injected into the tail vein of each lethally irradiated (1100 rads from a $^{137}$Cs source) B6-Ly5.2 female mouse along with $7.5\times10^5$ supporting bone marrow cells from un-irradiated B6-Ly5.2 mice. Starting from day 7 after transplantation, the recipient mice were treated with KPT-330 (20 mg/kg, dissolved in 2% DMSO/49% PEG300/ ddH$_2$O) or vehicle through oral gavage once every two days. KPT-330 was purchased from Selleck Chemicals.

Purification and Transduction of Mouse LSK Cells. LSK cells were purified from C57BL/6 mice as described previously (Vishwakarma et al., Leukemia 30(1): 200-208 (2016). Purified LSK cells were first cultured in medium [DMEM with 15% fetal bovine serum and murine Scf (100 ng/ml), Il-3 (6 ng/ml) and Il-6 (10 ng/ml)] for 24 hours to stimulate their proliferation, and subsequently infected twice in the same media with high-titer pMYs retroviruses on retronectin-coated plates for 48 hours.

Immunofluorescence. GFP-sorted LSK cells at 72 hours after retroviral transduction were fixed with 2% paraformaldehyde on poly-L-lysine coated microscope slides. The fixed cells were permeabilized with 0.05% Triton X-100, blocked with 10% normal goat serum and 1% BSA for 30 minutes. Cells were then incubated with anti-FLAG M2 (Sigma) at room temperature for 3 hours. After washing with PBS, cells were incubated with Alexa-Fluor 555 goat anti-mouse secondary antibody (Invitrogen) at room temperature for 1 hour. The nucleus was counter stained using DAPI and mounted with Fluoromount G (Electron Microscopy Sciences, Hatfield, PA). Images were acquired using a LSM 710 scanning confocal microscope (Zeiss, Germany).

Chromatin Immunoprecipitation. Mouse myeloid progenitors immortalized by 3×FLAG-tagged Setbp1 and Setbp1(D/N) were generated as described (Oakley et al., Blood 119(25): 6099-6108 (2012). ChIP analyses were performed using ChIP-IT Express kit (Active Motif, Carlsbad, CA). Immunoprecipitations were performed using anti-FLAG M2 (Sigma-Aldrich, St. Louis, MO), anti-XPO1 antibody (Novus Biological), mouse IgG (G3A1, 5415S, Cell Signaling Technologies, Danvers, MA), and rabbit IgG (2729S, Cell Signaling Technologies). Chromatin DNA was purified using Active Motif PCR Purification Kit (Active Motif) and quantified by real-time PCR. The ChIP primers used at the Hoxa9 promoter were described previously (Kuo et al., Cancer Cell 24(4): 423-437 (2013).

Western Blotting Analysis. For Western blotting analysis, whole cell lysates were prepared by direct lysis of cell pellets in heated 2×SDS sample buffer. Samples were resolved on 3-8% Tris-Acetate gels (Life Technologies, Carlsbad, CA) followed by transferring onto nitrocellulose membranes (Bio-Rad, Hercules, CA). Primary antibodies used include anti-Setbp1 (16841-1AP, Proteintech, Chicago, IL), anti-XPO1 (H-7, SC-374124, Santa Cruz Biotechnology, Dallas, TX), and anti-GAPDH (60004-1-Ig, Proteintech). Secondary antibodies used include goat anti-rabbit IgG-HRP ((7074S, Cell Signaling Technologies) and anti-mouse IgG-HRP (A-9044, Sigma Aldrich). Protein bands were visualized by incubation with SuperSignal West chemiluminescent substrate (Pierce, Thermo Fisher Scientific, Rockford, IL).

Real-Time RT-PCR. For real-time RT-PCR, total RNA was extracted from cells using Nucleospin RNA (Clontech, Duren, Germany). Oligo-dT-primed cDNA samples were prepared using Superscript III (Invitrogen), and real-time PCR analysis was performed in triplicates using SYBR green detection reagents (Invitrogen) on a QuantStudio real time PCR system (Applied Biosystems, Foster City, CA). Relative changes in expression were calculated according to the $\Delta\Delta Ct$ method. The cycling conditions were 50° C. for 2 minutes followed by 95° C. for 2 minutes, and then 40 cycles of 95° C. for 15 seconds and 60° C. for 1 minute. The following gene-specific primer sequences were used: Hoxa9 S, 5' TGT CTC CTC TCC CCC AAA CC 3'; Hoxa9 AS, 5' GAG ATG AGG CCT GGG ATTTAG A 3'; Hoxa10 S, 5' CCA GCC CTG GGT AAA CTT AGC 3'; Hoxa10 AS, 5' CATTGA CCT CAG GCC AGA CA 3'; Myb S, 5' CCA TGA AAG CTC GGG CTT AG 3'; Myb AS, 5' CTC GAC ATG GTG TCA GTT GTG 3'; β-Actin S, 5' CCT CCC TGG AGA AGA GCT A 3'; β-Actin AS, 5' TCC ATA CCC AAG AAG GAA G 3'; Gapdh S, 5' AGG TCG GTG TGA ACG GATTTG 3'; Gapdh AS, 5' TGTAGACCATGTAGTT-GAGGTCA 3'.

Statistical Analysis. Sample sizes and animal numbers were determined by previous experiences. No samples were excluded from analyses. All data were analyzed by two-tailed Student's t-test except that survival curves were compared by Log-rank test. The researchers were not blinded during sample collection and analysis.

Discussion

Figure 10:
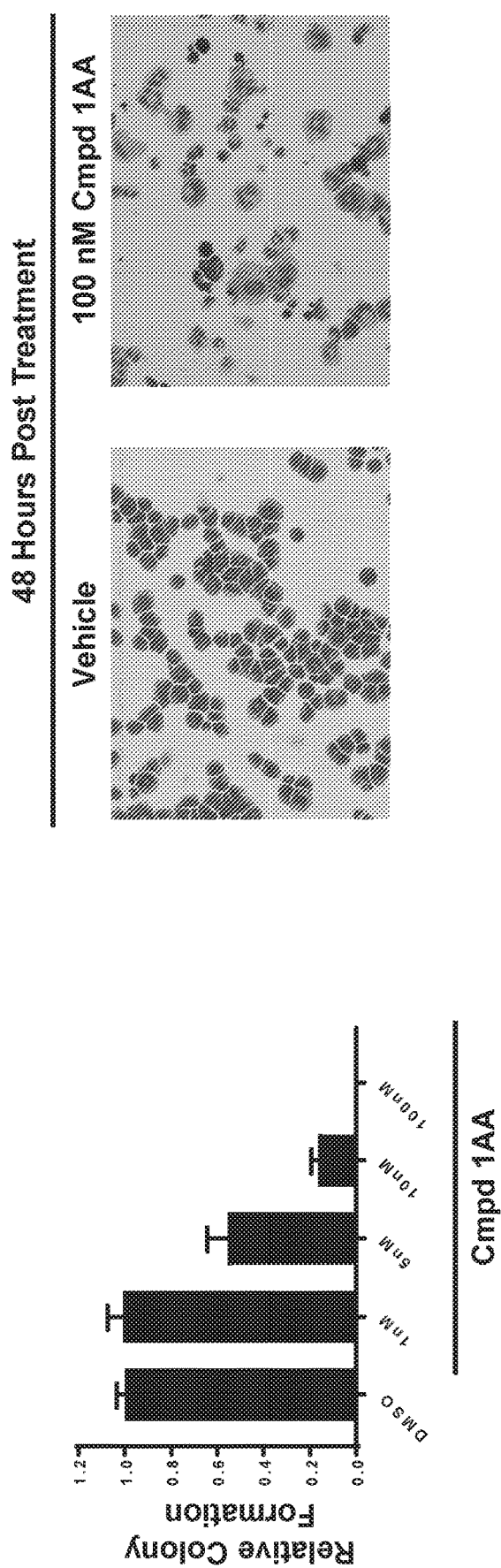
FIG. 10 shows that Compound (1AA) inhibits colony formation at concentrations of 1 nM, 5 nM, 10 nM, and 100 nM and induces differentiation/cytotoxicity in Setbp1-immortalized cells at 100 nM.
Figure 11:
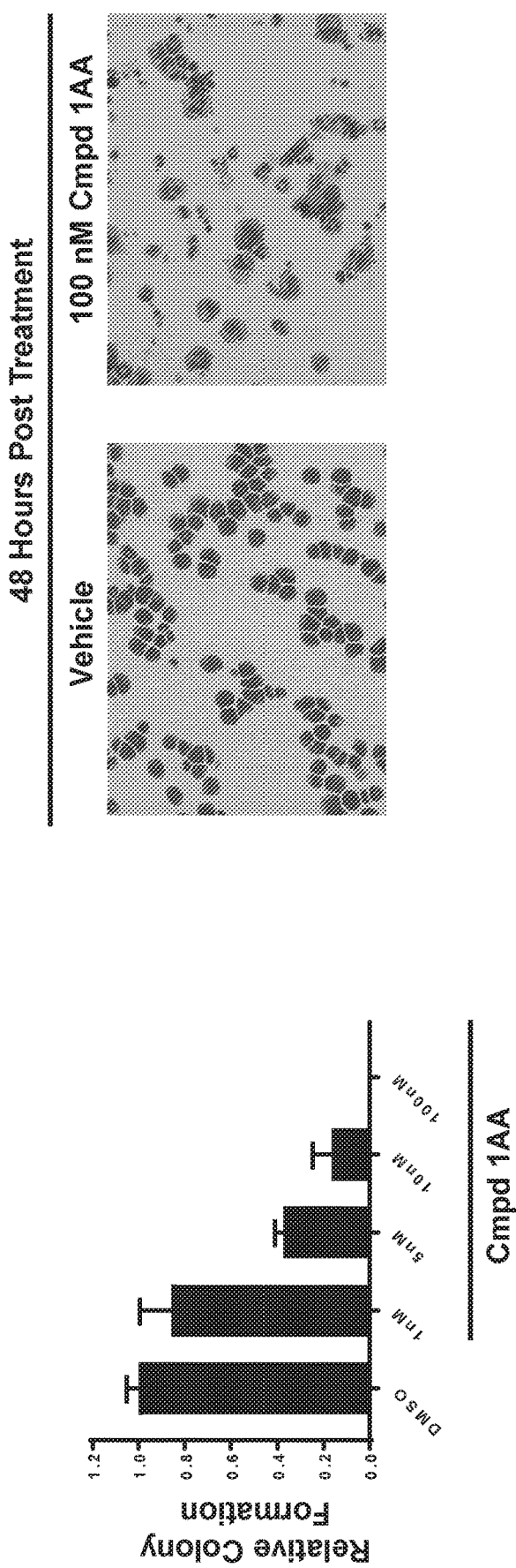
FIG. 11 shows that Compound (1AA) inhibits colony formation at concentrations of 1 nM, 5 nM, 10 nM, and 100 nM and induces differentiation/cytotoxicity in Setbp1 (D/N)-immortalized cells at 100 nM, where Setbp1 (D/N) is a Setbp1 mutant carrying a missense mutation identified frequently in patients of myeloid neoplasms.
Figure 12:
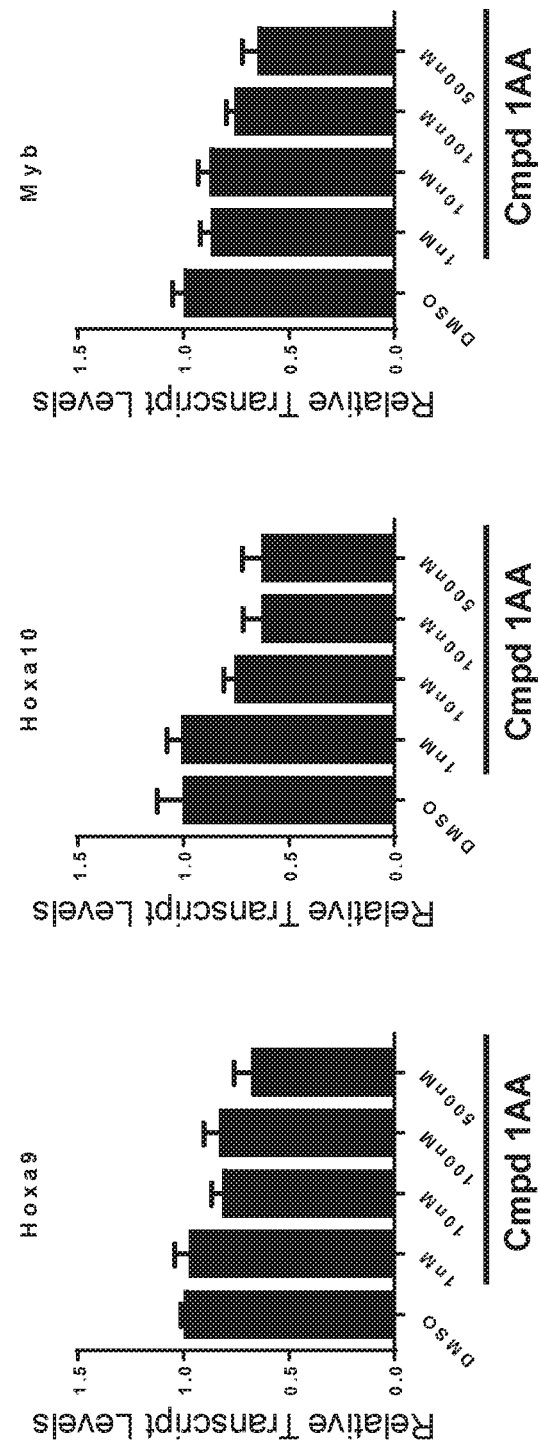
FIG. 12 shows that Compound (1AA) reduces Setbp1 target transcription levels of Hoxa9, Hoxa10 and Myb at 12 hours post-treatment at concentrations of 1 nM, 10 nM, 100 nM and 500 nM in Setbp1-immortalized cells.
Figure 13:
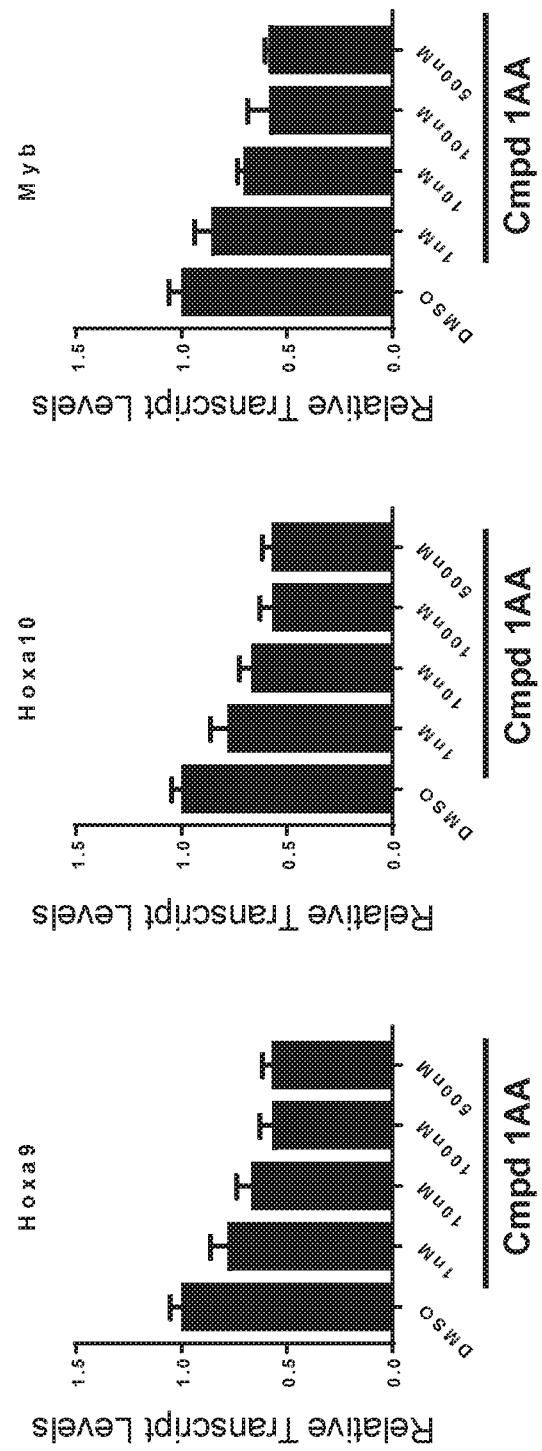
FIG. 13 shows that Compound (1AA) reduces Setbp1 (D/N) target transcription levels of Hoxa9, Hoxa10 and Myb at 12 hours post-treatment at concentrations of 1 nM, 10 nM, 100 nM and 500 nM in Setbp1 (D/N)-immortalized cells.

Compound (1AA) as a representative compound of Formula 1 was observed to inhibit colony formation and induce differentiation/cytotoxicity in Setbp1-immortalized cells (FIG. 10) and Setbp1(D/N)-immortalized cells (FIG. 11). In addition, Compound (1AA) reduced Setbp1 (FIG. 12) and Setbp1(D/N) (FIG. 13) target transcription levels of Hoxa9, Hoxa10 and Myb at 12 hours post-treatment in Setbp1-immortalized cells and Setbp1(D/N)-immortalized cells, respectively.

Compound (1AA) was also observed to disrupt the interaction between Setbp1(D/N) and XPO1 in HEK293T cells as expected from the design of the compound screen (FIG. 20). In addition, Compound (1AA) significantly reduced the spleen size and extended the survival of mice developing AML induced by Setbp1 activation (FIG. 21). Since XPO1 is ubiquitously expressed and SETBP1 has been detected in many tissues and cell types outside of hematopoietic system, it is highly possible that the survival and/or growth of many solid tumor types require their physical interaction and are therefore sensitive to Compound (1AA). The inhibitory activity of Compound (1AA) against solid tumors is being determined by assessing its growth inhibitory effects on human solid tumor cell lines in culture.

Figure 14:
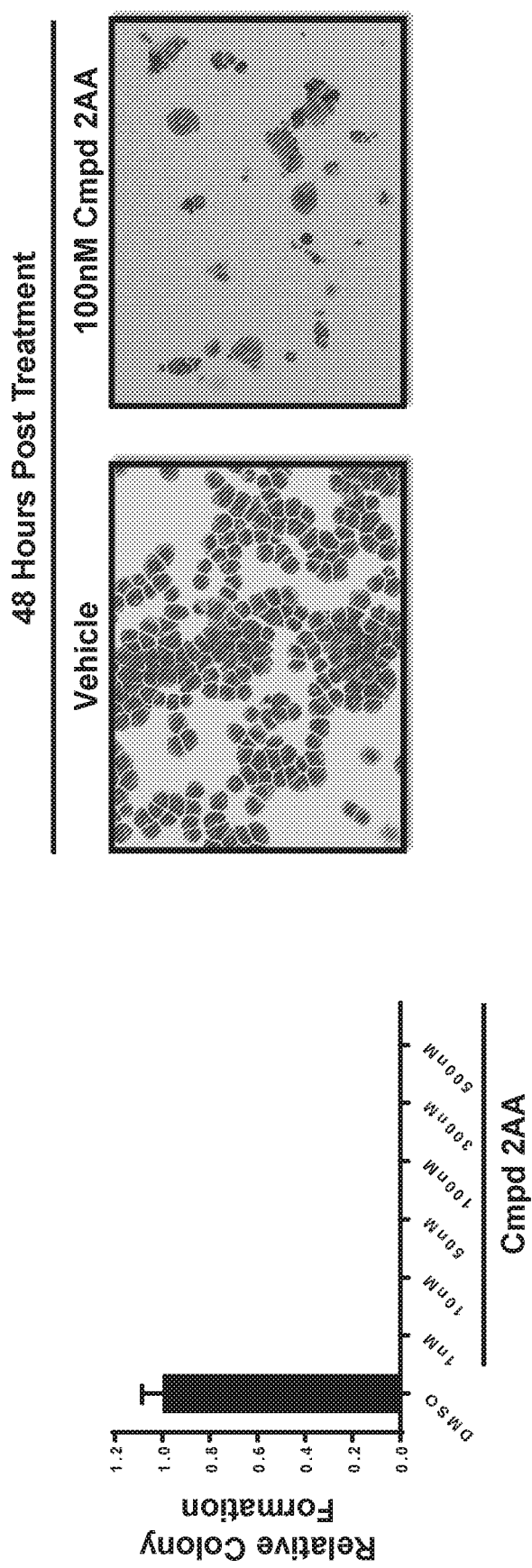
FIG. 14 shows that Compound (2AA) inhibits colony formation at concentrations of 1 nM, 5 nM, 10 nM, and 100 nM and induces differentiation/cytotoxicity in Setbp1-immortalized cells at 100 nM.
Figure 15:
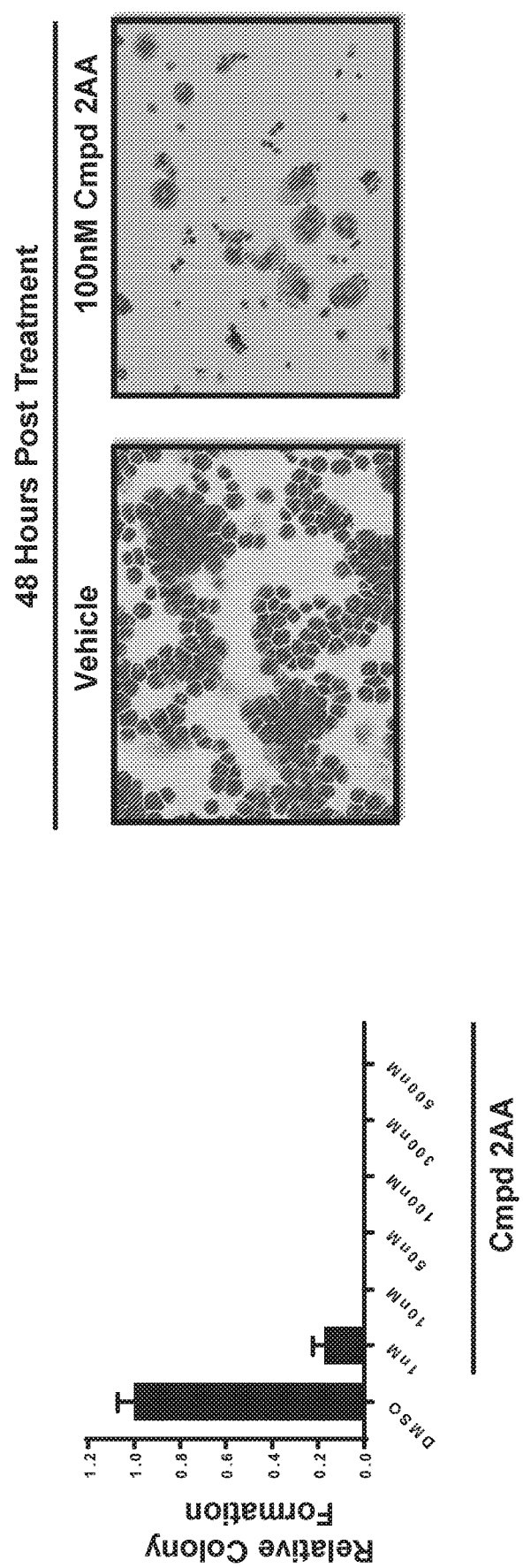
FIG. 15 shows that Compound (2AA) inhibits colony formation at 1 nM, 10 nM, 50 nM, 100 nM, 300 nM and 500 nM concentration and induces differentiation/cytotoxicity in Setbp1 (D/N)-immortalized cells at 100 nM.
Figure 16:
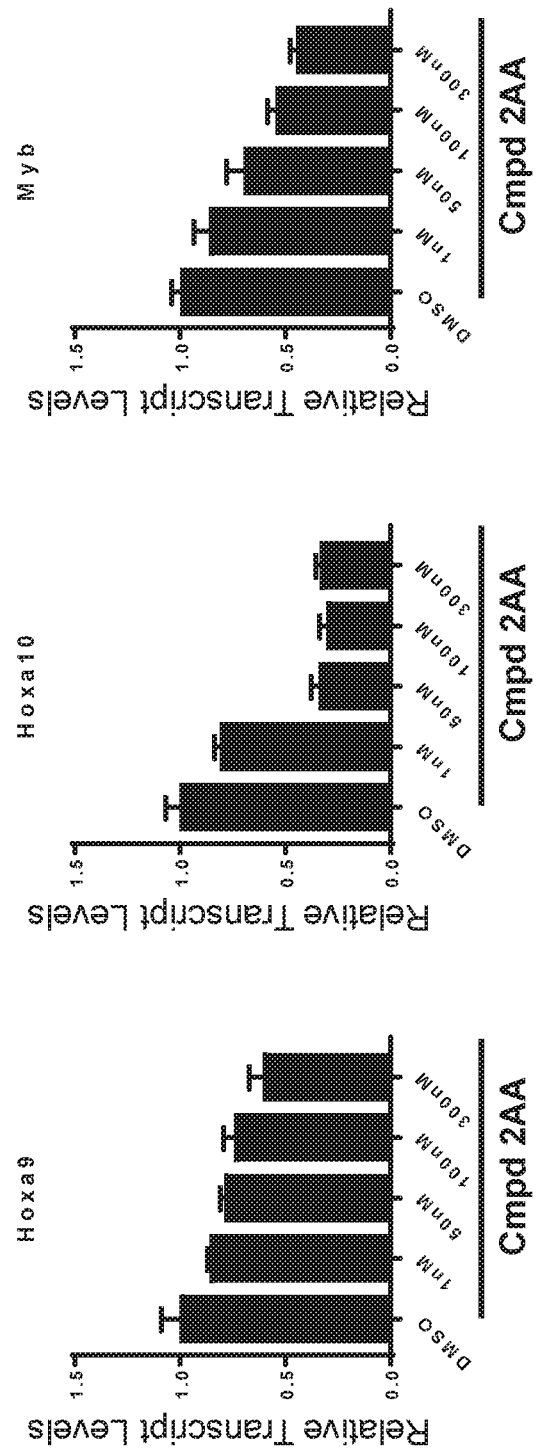
FIG. 16 shows that Compound (2AA) reduces Setbp1 target transcription levels of Hoxa9, Hoxa10 and Myb at 12 hours post-treatment at concentrations of 1 nM, 50 nM, 100 nM and 300 nM in Setbp1-immortalized cells.

Compound (2AA) as a representative compound of Formula 2 was observed to inhibit colony formation and induce differentiation/cytotoxicity in Setbp1-immortalized cells (FIG. 14) and Setbp1(D/N)-immortalized cells (FIG. 15). In addition, Compound (2AA) reduced Setbp1 (FIG. 16) and Setbp1(D/N) (FIG. 17) target transcription levels of Hoxa9, Hoxa10 and Myb at 12 hours post-treatment in Setbp1-immortalized cells and Setbp1(D/N)-immortalized cells, respectively.

All patents and publications cited herein are incorporated by reference in their entireties.

What is claimed is:

1. A method for treating a myeloid neoplasm or a solid tumor in a subject, comprising administering to the subject a therapeutically effective amount of a compound, wherein the compound is:

a compound of Formula (1):

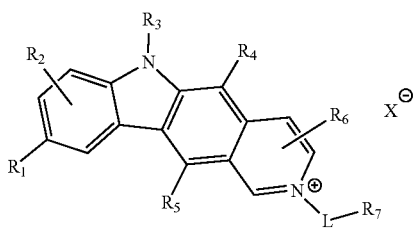

wherein:
$R_1$ is —$OR_8$;
$R_2$, $R_3$ and $R_6$ are H;
$R_4$ and $R_5$ are independently $C_{1-4}$ alkyl;
$R_7$ is —$NR_{10}R_{10}$ or a piperidinyl group;
L is —$(CR_9R_9)_n$—;
$X^-$ is an organic or inorganic anion;
$R_8$ is H or $C_{1-3}$ alkyl;
each $R_9$ is independently H or $C_{1-3}$ alkyl;
each $R_{10}$ is independently H or $C_{1-3}$ alkyl; and
n is 1, 2, 3 or 4; or a compound of Formula (2A):

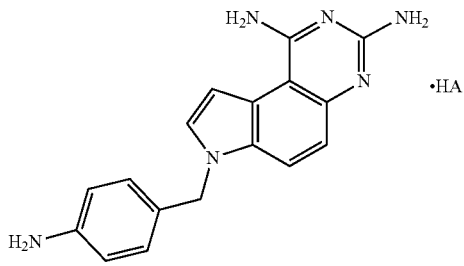 [SMILES: Nc1ccc(Cn2ccc3c4c(N)nc(N)nc4ccc32)cc1 ; "·HA"]

where HA is a proton donor,
wherein the myeloid neoplasm is selected from the group consisting of acute myeloid leukemia (AML), chronic myelomonocytic leukemia (CMML), juvenile myelomonocytic leukemia (JMML), chronic myeloid leukemia blast crisis (CML-BC), atypical chronic myeloid leukemia (aCML), secondary acute myeloid leukemia (sAML), myelodysplastic syndrome (MDS), and chronic neutrophilic leukemia (CNL).

2. The method according to claim 1, wherein X is selected from the group consisting of F, Cl, Br and I.

3. The method according to claim 1, wherein
$R_1$ is —$OR_8$;
$R_2$, $R_3$, $R_6$, $R_8$ and $R_9$ are H;
$R_4$ and $R_5$ are $CH_3$;
$R_7$ is a piperidinyl group;
L is —$(CR_9R_9)_n$—;
X is selected from the group consisting of F, Cl, Br and I; and
n is 1, 2, 3 or 4.

4. The method according to claim 1, wherein
$R_1$ is —$OR_8$;
$R_2$, $R_3$, $R_6$, $R_8$ and $R_9$ are H;
$R_4$ and $R_5$ are $CH_3$;
$R_7$ is —$NR_{10}R_{10}$;
each $R_{10}$ is independently $C_{1-3}$ alkyl;
L is —$(CR_9R_9)_n$—;
X is selected from the group consisting of F, Cl, Br and I; and
n is 1, 2, 3 or 4.

5. The method according to claim 1, wherein the compound of Formula (1) is a compound of Formula (1A):

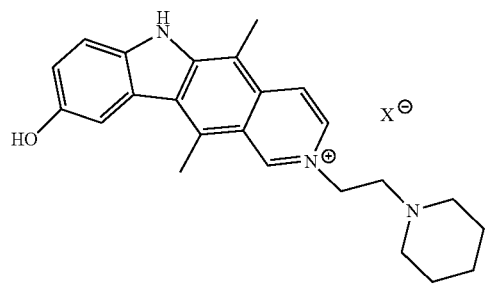

where X is selected from the group consisting of F, Cl, Br and I.

6. The method according to claim 1, wherein the compound of Formula (1) is Compound (1AA):

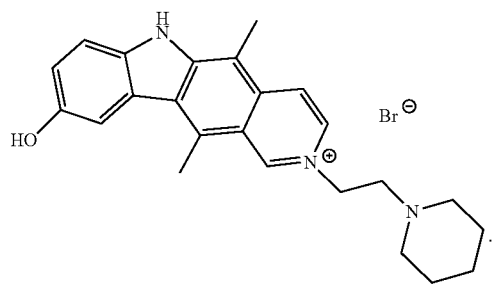 [SMILES: Cc1c2cc[n+](CCN3CCCCC3)cc2c(C)c2c1[nH]c1ccc(O)cc12 ; [Br-]]

7. The method according to claim 1, wherein the compound of Formula (1) is a compound of Formula (1B):

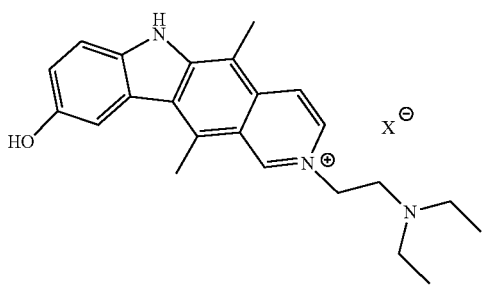

where X is selected from the group consisting of F, Cl, Br and I.

8. The method according to claim 1, wherein the compound of Formula (1) is Compound (1BB):

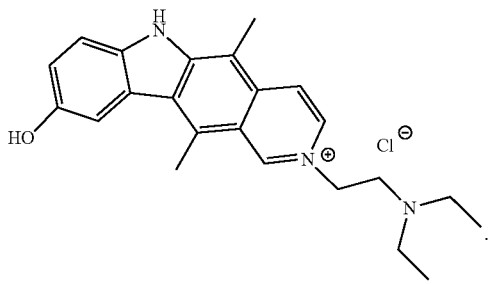 [SMILES: CCN(CC)CC[n+]1ccc2c(C)c3[nH]c4ccc(O)cc4c3c(C)c2c1 ; [Cl-]]

9. The method according to claim 1, wherein HA is selected from the group consisting of hydrochloric acid, hydrobromic acid, sulfuric acid, phosphoric acid, and nitric acid.

10. The method according to claim 1, wherein the compound of Formula (2A) is Compound (2AA):

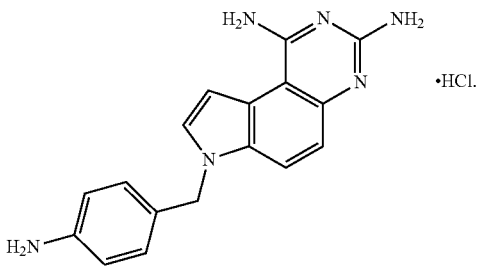 [SMILES: Nc1ccc(Cn2ccc3c4c(N)nc(N)nc4ccc32)cc1]

11. The method according to claim 1, wherein the myeloid neoplasm or the solid tumor is associated with SETBP1 activation.

12. The method according to claim 1, wherein the solid tumor is selected from the group consisting of breast, colorectal, lung, ovarian, prostate, skin, liver, pancreatic, kidney, endometrium, esophagus, gastric, and head and neck cancers.

13. The method according to claim 1, wherein the compound is present in a pharmaceutical composition comprising one or more excipients.

* * * * *